(12) United States Patent
Miyazaki et al.

(10) Patent No.: US 12,007,458 B2
(45) Date of Patent: Jun. 11, 2024

(54) MAGNETIC RESONANCE IMAGING APPARATUS AND MAGNETIC RESONANCE IMAGING METHOD

(71) Applicants: CANON MEDICAL SYSTEMS CORPORATION, Otawara (JP); The Regents of the University of California, Oakland, CA (US)

(72) Inventors: Mitsue Miyazaki, Des Plaines, IL (US); Christine Chung, Oakland, CA (US)

(73) Assignees: CANON MEDICAL SYSTEMS CORPORATION, Otawara (JP); The Regents of the University of California, Oakland, CA (US)

( * ) Notice: Subject to any disclaimer, the term of this patent is extended or adjusted under 35 U.S.C. 154(b) by 398 days.

(21) Appl. No.: 16/504,455

(22) Filed: Jul. 8, 2019

(65) Prior Publication Data

US 2021/0011103 A1 Jan. 14, 2021

(51) Int. Cl.
*G01R 33/48* (2006.01)
*A61B 5/055* (2006.01)
(Continued)

(52) U.S. Cl.
CPC .......... *G01R 33/4828* (2013.01); *A61B 5/055* (2013.01); *G01R 33/50* (2013.01); *G01R 33/543* (2013.01); *G01R 33/546* (2013.01)

(58) Field of Classification Search
CPC .... A61B 5/055; G01R 33/4828; G01R 33/50; G01R 33/543; G01R 33/546
See application file for complete search history.

(56) References Cited

U.S. PATENT DOCUMENTS 4,806,866 A * 2/1989 Maier ................ G01R 33/4833
324/313
5,225,781 A * 7/1993 Glover ................ G01R 33/485
324/309
(Continued)

FOREIGN PATENT DOCUMENTS

JP 2010-502302 A 1/2010
JP 2012-090867 5/2012
JP 2014-008173 A 1/2014

OTHER PUBLICATIONS

Xu, K. et al. "Reliable Quantification of Marrow Fat Content and Unsaturation Level Using in Vivo MR Spectroscopy", Magn Reson Med. 79 (3), 2018, 20 pages.
(Continued)

*Primary Examiner* — Steven L Yeninas
(74) *Attorney, Agent, or Firm* — Oblon, McClelland, Maier & Neustadt, L.L.P.

(57) ABSTRACT

A magnetic resonance imaging apparatus according to an embodiment includes sequence controlling circuitry and processing circuitry. The sequence controlling circuitry acquires a first piece of data by executing a first pulse sequence having a first Echo Time (TE) value, to acquire a second piece of data by executing a second pulse sequence having a second TE value different from the first TE value, and to acquire a third piece of data by executing a third pulse sequence having a third TE value different from the first and the second TE values. The processing circuitry extracts a signal related to water, a signal related to a first fat, and a signal related to a second fat, on the basis of the first piece of data, the second piece of data, and the third piece of data.

15 Claims, 12 Drawing Sheets

(51) Int. Cl.
*G01R 33/50* (2006.01)
*G01R 33/54* (2006.01)

(56) References Cited

U.S. PATENT DOCUMENTS

| | | | | |
|---|---|---|---|---|
| 5,321,359 A * | 6/1994 | Schneider | .......... | G01R 33/4828 |
| | | | | 324/309 |
| 5,594,336 A * | 1/1997 | Gullapalli | .......... | G01R 33/4828 |
| | | | | 324/309 |
| 5,757,188 A * | 5/1998 | Miyazaki | .......... | G01R 33/4828 |
| | | | | 324/309 |
| 5,891,032 A * | 4/1999 | Harvey | .............. | G01R 33/4828 |
| | | | | 324/309 |
| 7,202,665 B1 * | 4/2007 | Reeder | .............. | G01R 33/4824 |
| | | | | 324/309 |
| 9,714,999 B1 | 7/2017 | Nakai et al. | | |
| 2005/0215882 A1 * | 9/2005 | Chenevert | .......... | G01R 33/4828 |
| | | | | 600/410 |
| 2008/0048657 A1 | 2/2008 | Reeder | | |
| 2008/0048659 A1 | 2/2008 | Reeder | | |
| 2009/0261823 A1 * | 10/2009 | Yu | ...................... | G01R 33/4828 |
| | | | | 324/307 |
| 2010/0013478 A1 * | 1/2010 | Abe | .................. | G01R 33/4828 |
| | | | | 324/309 |
| 2010/0195885 A1 * | 8/2010 | Ma | ........................ | G16H 30/40 |
| | | | | 382/131 |
| 2010/0201361 A1 * | 8/2010 | Edelman | .............. | G01R 33/286 |
| | | | | 324/309 |
| 2011/0267060 A1 * | 11/2011 | Abe | .................. | G01R 33/4828 |
| | | | | 324/318 |
| 2012/0256625 A1 * | 10/2012 | Block | ................ | G01R 33/4828 |
| | | | | 324/309 |
| 2013/0088226 A1 * | 4/2013 | Miyazaki | ........... | G01R 33/5607 |
| | | | | 324/309 |
| 2013/0249552 A1 * | 9/2013 | Imamura | ............ | G01R 33/4828 |
| | | | | 324/309 |
| 2015/0185304 A1 * | 7/2015 | Wang | ................ | G01R 33/4828 |
| | | | | 324/309 |
| 2015/0309137 A1 * | 10/2015 | Bydder | .................. | A61B 5/055 |
| | | | | 324/309 |
| 2018/0217216 A1 * | 8/2018 | Suh | .................... | G01R 33/5601 |
| 2020/0256940 A1 * | 8/2020 | Grodzki | ............... | G01R 33/543 |
| 2020/0278406 A1 * | 9/2020 | Sharma | .............. | G01R 33/4828 |
| 2020/0309884 A1 * | 10/2020 | Bekku | ................ | G01R 33/4828 |

OTHER PUBLICATIONS

Reeder, S. et al. "Homodyne Reconstruction and Ideal Water-Fat Decomposition", Magnetic Resonance in Medicine 54, 2005, pp. 586-593.

Yu, H. et al. "*Multiecho Water-Fat Separation and Simultaneous $R_2$ Estimation with Multifrequency Fat Spectrum Modeling*", Magnetic Resonance in Medicine 60, 2008, pp. 1122-1134.

Hamilton, G. et al. "MR Properties of Brown and White Adipose Tissues", Journal of Magnetic Resonance Imaging 34, 2011, pp. 468-473.

Office Action issued Jun. 20, 2023, in corresponding Japanese Patent Application No. 2020-046052, 4 pages.

Japanese Office Action issued Oct. 3, 2023 in Japanese Patent Application No. 2020-046052, 3 pages.

* cited by examiner

1/2 τ time

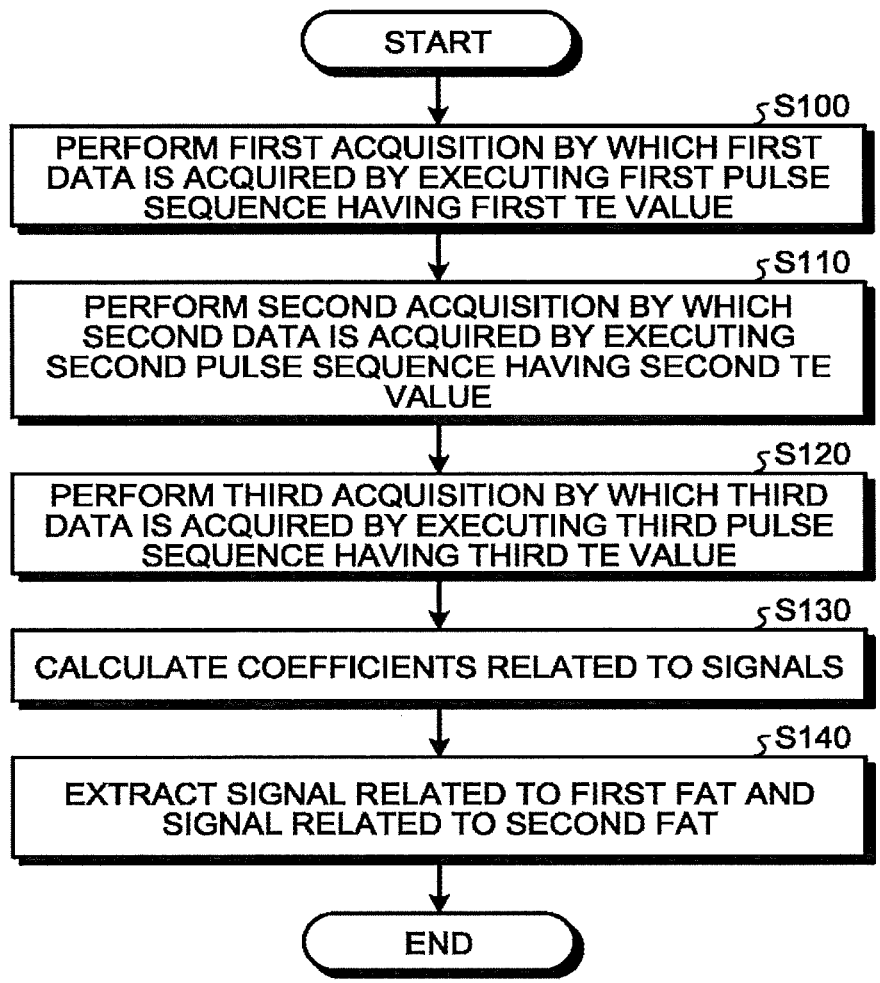

FIRST ACQUISITION

SECOND ACQUISITION

THIRD ACQUISITION

FIRST ACQUISITION

SECOND ACQUISITION

THIRD ACQUISITION

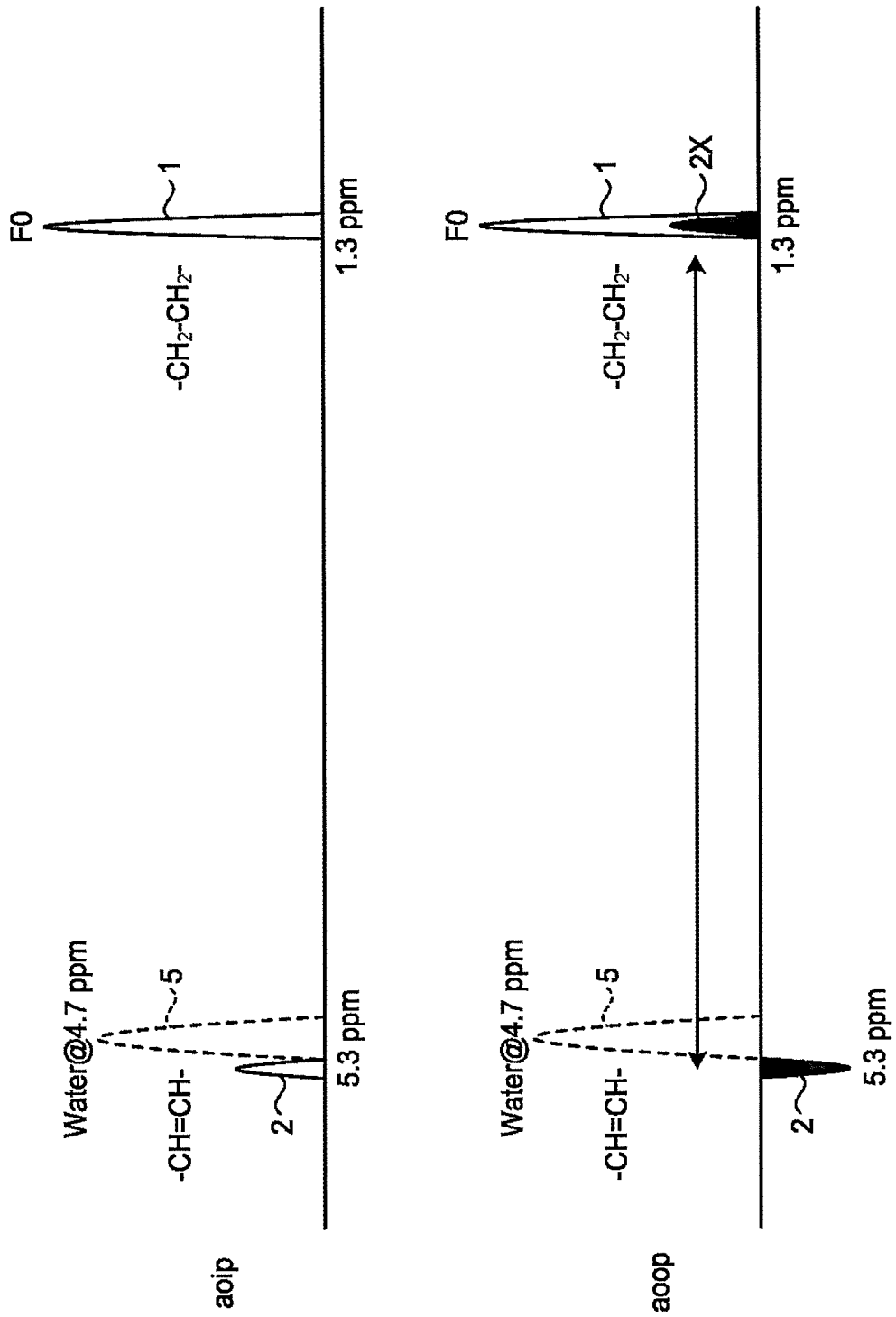

FIRST ACQUISITION

SECOND ACQUISITION

THIRD ACQUISITION

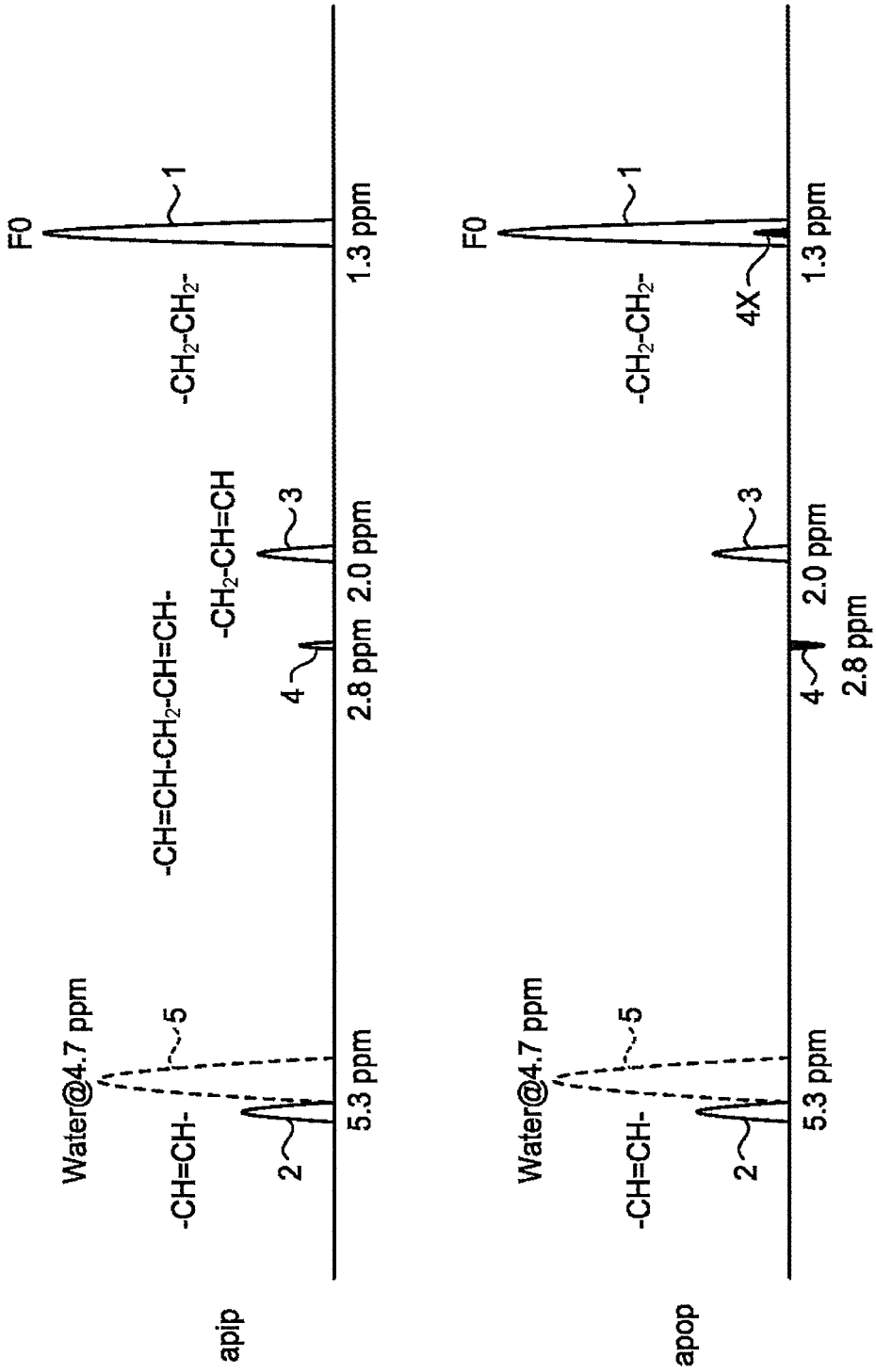

MAGNETIC RESONANCE IMAGING APPARATUS AND MAGNETIC RESONANCE IMAGING METHOD

FIELD

Embodiments described herein relate generally to a magnetic resonance imaging apparatus and a magnetic resonance imaging method.

BACKGROUND

Separating a signal of water and a signal of fat from each other is an important issue in magnetic resonance imaging. In recent years, some focus is placed on fats such as olefinic fat that is other than saturated fats. For example, people have an interest in the amount of olefinic fat in the liver, bones, and various fat tissues.

To quantify signals of saturated fat and unsaturated fat, Point Resolved Spectroscopy (PRESS) may be used, for example, by which an image taking process is performed by implementing single-voxel Magnetic Resonance Spectroscopy (MRS). However, it is desirable to quantify fats by using a two-dimensional (2D) or three-dimensional (3D) image, instead of the single-voxel image taking process.

Further, for example, a known method for extracting a signal of fat uses a method called Iterative Decomposition of water and fat with Echo Asymmetry and Least-squares estimation (IDEAL), or the like. According to this method, however, an image taking process is usually performed on the assumption that the number of types of fat to be rendered is one.

BRIEF DESCRIPTION OF THE DRAWINGS

FIG. 4 is a flowchart for explaining a process performed by a magnetic resonance imaging apparatus according to embodiments;

FIGS. 7, 8A, 8B, 8C, 8D, 9, and 10 are drawings for explaining processes performed by a magnetic resonance imaging apparatus according to a third embodiment.

DETAILED DESCRIPTION

First Embodiment

A magnetic resonance imaging apparatus according to an embodiment includes sequence controlling circuitry and processing circuitry. The sequence controlling circuitry acquires a first piece of data by executing a first pulse sequence having a first Echo Time (TE) value, to acquire a second piece of data by executing a second pulse sequence having a second TE value different from the first TE value, and to acquire a third piece of data by executing a third pulse sequence having a third TE value different from the first and the second TE values. The processing circuitry extracts a signal related to water, a signal related to a first fat, and a signal related to a second fat, on the basis of the first piece of data, the second piece of data, and the third piece of data.

Figure 1:
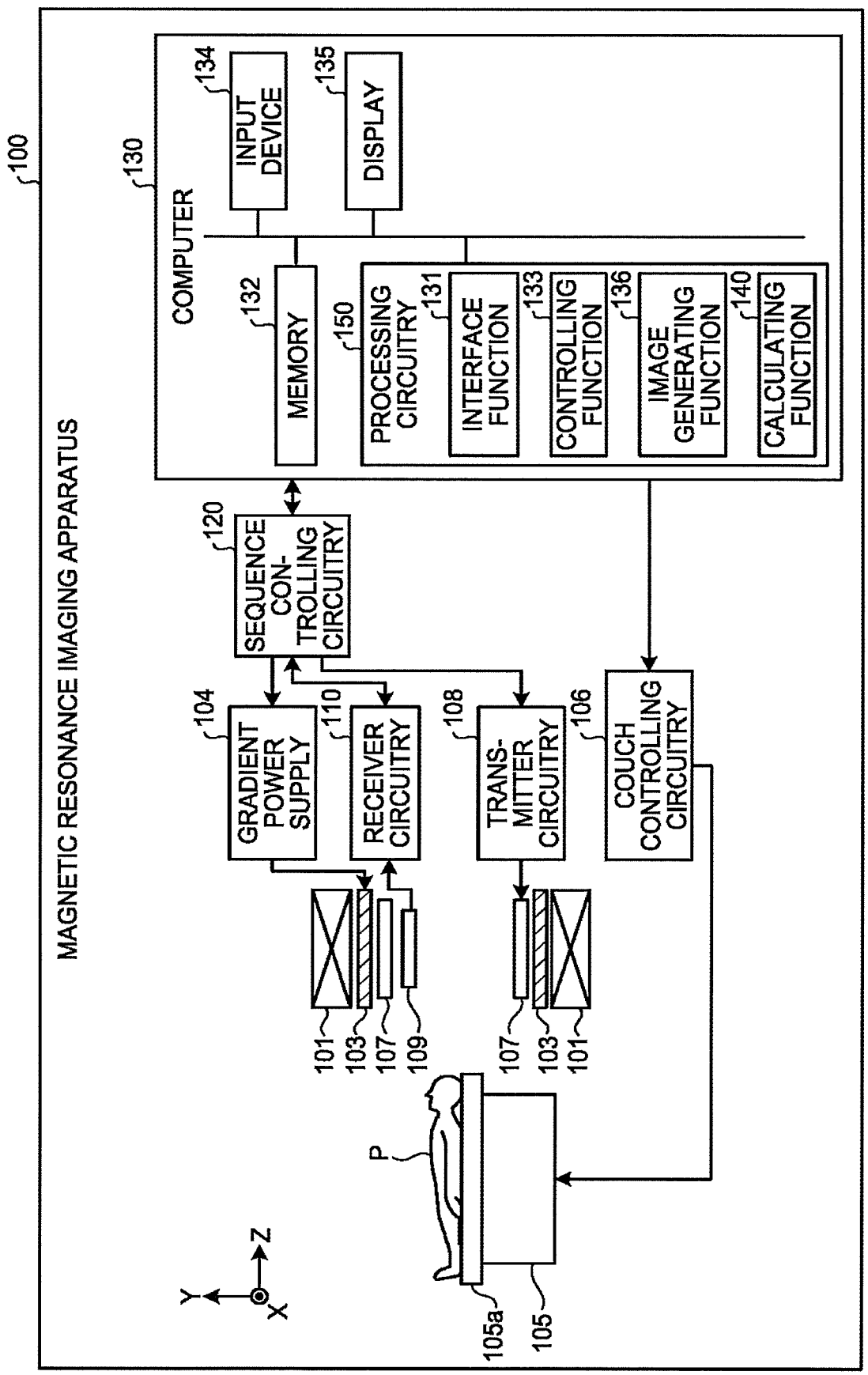
FIG. 1 is a diagram illustrating a magnetic resonance imaging apparatus according to an embodiment.

FIG. 1 is a block diagram illustrating a magnetic resonance imaging apparatus 100 according to an embodiment. As illustrated in FIG. 1, the magnetic resonance imaging apparatus 100 includes a static magnetic field magnet 101, a static magnetic field power supply (not illustrated), a gradient coil 103, a gradient power supply 104, a couch 105, couch controlling circuitry 106, a transmitter coil 107, transmitter circuitry 108, a receiver coil 109, receiver circuitry 110, sequence controlling circuitry 120 (a sequence controlling unit), and a computer 130 (which may also be referred to as an "image processing apparatus"). The magnetic resonance imaging apparatus 100 does not include an examined subject (hereinafter "patient") P (e.g., a human body). Further, the configuration illustrated in FIG. 1 is merely an example. For instance, one or more of the constituent elements of the sequence controlling circuitry 120 and the computer 130 may be integrated together or separated from the other elements, as appropriate.

The static magnetic field magnet 101 is a magnet formed to have a hollow and substantially circular cylindrical shape and configured to generate a static magnetic field in the space on the inside thereof. For example, the static magnetic field magnet 101 may be a superconductive magnet or the like and is configured to cause magnetic excitation by receiving a supply of an electric current from the static magnetic field power supply. The static magnetic field power supply is configured to supply the electric current to the static magnetic field magnet 101. Alternatively, the static magnetic field magnet 101 may be a permanent magnet. In that situation, the magnetic resonance imaging apparatus 100 does not necessarily have to include the static magnetic field power supply. Further, the static magnetic field power supply may be provided separately from the magnetic resonance imaging apparatus 100.

The gradient coil 103 is a coil formed to have a hollow and substantially circular cylindrical shape and is disposed on the inside of the static magnetic field magnet 101. The gradient coil 103 is structured by combining together three coils corresponding to X-, Y-, and Z-axes that are orthogonal to one another. By individually receiving a supply of an electric current from the gradient power supply 104, these three coils are configured to generate gradient magnetic fields of which the magnetic field intensities change along the X-, Y-, and Z-axes respectively. The gradient magnetic fields generated along the X-, Y-, and Z-axes by the gradient coil 103 are, for example, a slice gradient magnetic field Gs, a phase-encoding gradient magnetic field Ge, and a read-out gradient magnetic field Gr. The gradient power supply 104 is configured to supply the electric currents to the gradient coil 103.

The couch 105 includes a couchtop 105a on which the patient P is placed. Under control of the couch controlling circuitry 106, the couchtop 105a is inserted to the inside of a hollow space (an image taking opening) of the gradient coil 103, while the patient P is placed thereon. Usually, the couch 105 is installed in such a manner that the longitudinal direction thereof extends parallel to the central axis of the static magnetic field magnet 101. Under control of the computer 130, the couch controlling circuitry 106 is configured to move the couchtop 105a in longitudinal directions and up-and-down directions by driving the couch 105.

The transmitter coil 107 is disposed on the inside of the gradient coil 103 and is configured to generate a radio frequency magnetic field by receiving a supply of a Radio Frequency (RF) pulse from the transmitter circuitry 108. The transmitter circuitry 108 is configured to supply the transmitter coil 107 with the RF pulse corresponding to a Larmor frequency determined by the type of the targeted atom and intensities of magnetic fields.

The receiver coil 109 is disposed on the inside of the gradient coil 103 and is configured to receive magnetic resonance signals (which hereinafter may be referred to as "MR signals" as necessary) emitted from the patient P due to an influence of the radio frequency magnetic field. When having received the magnetic resonance signals, the receiver coil 109 outputs the received magnetic resonance signals to the receiver circuitry 110.

The transmitter coil 107 and the receiver coil 109 described above are merely examples. One or more coils may be configured by selecting one or combining two or more from among the following: a coil having only a transmitting function; a coil having only a receiving function; and a coil having transmit and receiver functions.

The receiver circuitry 110 is configured to detect the magnetic resonance signals output from the receiver coil 109 and to generate magnetic resonance data on the basis of the detected magnetic resonance signals. More specifically, the receiver circuitry 110 generates the magnetic resonance data by performing a digital conversion on the magnetic resonance signals output from the receiver coil 109. Further, the receiver circuitry 110 is configured to transmit the generated magnetic resonance data to the sequence controlling circuitry 120. The receiver circuitry 110 may be provided on the side of a gantry device where the static magnetic field magnet 101, the gradient coil 103, and the like are provided.

The sequence controlling circuitry 120 is configured to perform an image taking process on the patient P by driving the gradient power supply 104, the transmitter circuitry 108, and the receiver circuitry 110 on the basis of sequence information transmitted thereto from the computer 130. In this situation, the sequence information is information defining a procedure for performing the image taking process. The sequence information defines: the intensity of the electric current to be supplied from the gradient power supply 104 to the gradient coil 103 and the timing with which the electric current is to be supplied; the intensity of the RF pulse to be supplied from the transmitter circuitry 108 to the transmitter coil 107 and the timing with which the RF pulse is to be applied; the timing with which the magnetic resonance signals are to be detected by the receiver circuitry 110, and the like. For example, the sequence controlling circuitry 120 may be an integrated circuit such as an Application Specific Integrated Circuit (ASIC), a Field Programmable Gate Array (FPGA), or the like or an electronic circuit such as a Central Processing Unit (CPU), a Micro Processing Unit (MPU), or the like. Details of a pulse sequence executed by the sequence controlling circuitry 120 will be explained later.

Further, when having received the magnetic resonance data from the receiver circuitry 110 as a result of performing the image taking process on the patient P by driving the gradient power supply 104, the transmitter circuitry 108, and the receiver circuitry 110, the sequence controlling circuitry 120 is configured to transfer the received magnetic resonance data to the computer 130.

The computer 130 is configured to exercise overall control of the magnetic resonance imaging apparatus 100 and to generate images, and the like. The computer 130 includes a memory 132, an input device 134, a display device 135, and processing circuitry 150. The processing circuitry 150 includes an interface function 131, a controlling function 133, an image generating function 136, and a calculating function 140.

In an embodiment, processing functions performed by the interface function 131, the controlling function 133, the image generating function 136, and the calculating function 140 are stored in the memory 132 in the form of computer-executable programs. The processing circuitry 150 is a processor configured to realize the functions corresponding to the programs by reading and executing the programs from the memory 132. In other words, the processing circuitry 150 that has read the programs has the functions illustrated within the processing circuitry 150 in FIG. 1. FIG. 1 illustrates an example in which the single processing circuitry (i.e., the processing circuitry 150) realizes the processing functions performed by the interface function 131, the controlling function 133, the image generating function 136, and the calculating function 140; however, another arrangement is also acceptable in which the processing circuitry 150 is structured by combining together a plurality of independent processors, so that the functions are realized as a result of the processors executing the programs. In other words, it is acceptable to configure each of the functions described above as a program, so that the single processing circuit (i.e., the processing circuitry 150) executes the programs. Alternatively, one or more specific functions each may be installed in a dedicated independent program-executing circuit. The interface function 131, the controlling function 133, the image generating function 136, and the calculating function 140 are examples of a receiving unit, a controlling unit, an image generating unit, and a calculating unit, respectively. The sequence controlling circuitry 120 is an example of a sequence controlling unit. Specific processes performed by the calculating function 140 will be explained later.

The term "processor" used in the above explanation denotes, for example, a Central Processing Unit (CPU), a Graphical Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs stored in the memory 132.

Further, instead of saving the programs in the memory 132, it is also acceptable to directly incorporate the programs in the circuits of the processors. In that situation, the processors realize the functions thereof by reading and executing the programs incorporated in the circuits thereof. Similarly, the couch controlling circuitry 106, the transmitter circuitry 108, the receiver circuitry 110, and the like are also each configured with an electronic circuit such as the processor defined above.

By employing the interface function 131, the processing circuitry 150 is configured to transmit the sequence information to the sequence controlling circuitry 120 and to receive the magnetic resonance data from the sequence controlling circuitry 120. When having received the magnetic resonance data, the processing circuitry 150 including the interface function 131 is configured to store the received magnetic resonance data into the memory 132.

The magnetic resonance data stored in the memory 132 is arranged into a k-space by the controlling function 133. As a result, the memory 132 stores therein k-space data.

The memory 132 is configured to store therein the magnetic resonance data received by the processing circuitry 150 having the interface function 131; the k-space data arranged into the k-space by the processing circuitry 150 having the controlling function 133; image data generated by the processing circuitry 150 having the image generating function 136; and the like. For example, the memory 132 is configured with a semiconductor memory element such as a Random Access Memory (RAM), a flash memory, or the like, or a hard disk, an optical disk, or the like.

The input device 134 is configured to receive inputs of various types of instructions and information from the operator. The input device 134 is, for example, a pointing device such as a mouse and/or a trackball; a selecting device such as a mode changing switch; and/or an input device such as a keyboard. The display device 135 is configured to display, under control of the processing circuitry 150 having the controlling function 133, a Graphical User Interface (GUI) used for receiving inputs of image taking conditions, as well as images generated by the processing circuitry 150 having the image generating function 136, and the like. The display device 135 is, for example, a display device configured with a liquid crystal display monitor, or the like.

By employing the controlling function 133, the processing circuitry 150 is configured to control image taking processes, image generating processes, image display processes, and the like, by exercising overall control of the magnetic resonance imaging apparatus 100. For example, the processing circuitry 150 having the controlling function 133 receives an input of an image taking condition (e.g., an image taking parameter or the like) via the GUI and generates sequence information according to the received image taking condition. Further, the processing circuitry 150 having the controlling function 133 transmits the generated sequence information to the sequence controlling circuitry 120.

By employing the image generating function 136, the processing circuitry 150 is configured to generate an image by reading the k-space data from the memory 132 and performing a reconstructing process such as a Fourier transform on the read k-space data.

Next, a background of the magnetic resonance imaging apparatus 100 according to an embodiment will briefly be explained.

Separating a signal of water and a signal of fat from each other is an important issue in magnetic resonance imaging. In recent years, some focus is placed on fats such as olefinic fat that is other than saturated fats. For example, people have an interest in the amount of olefinic fat in the liver, bones, and various fat tissues.

Figure 2:
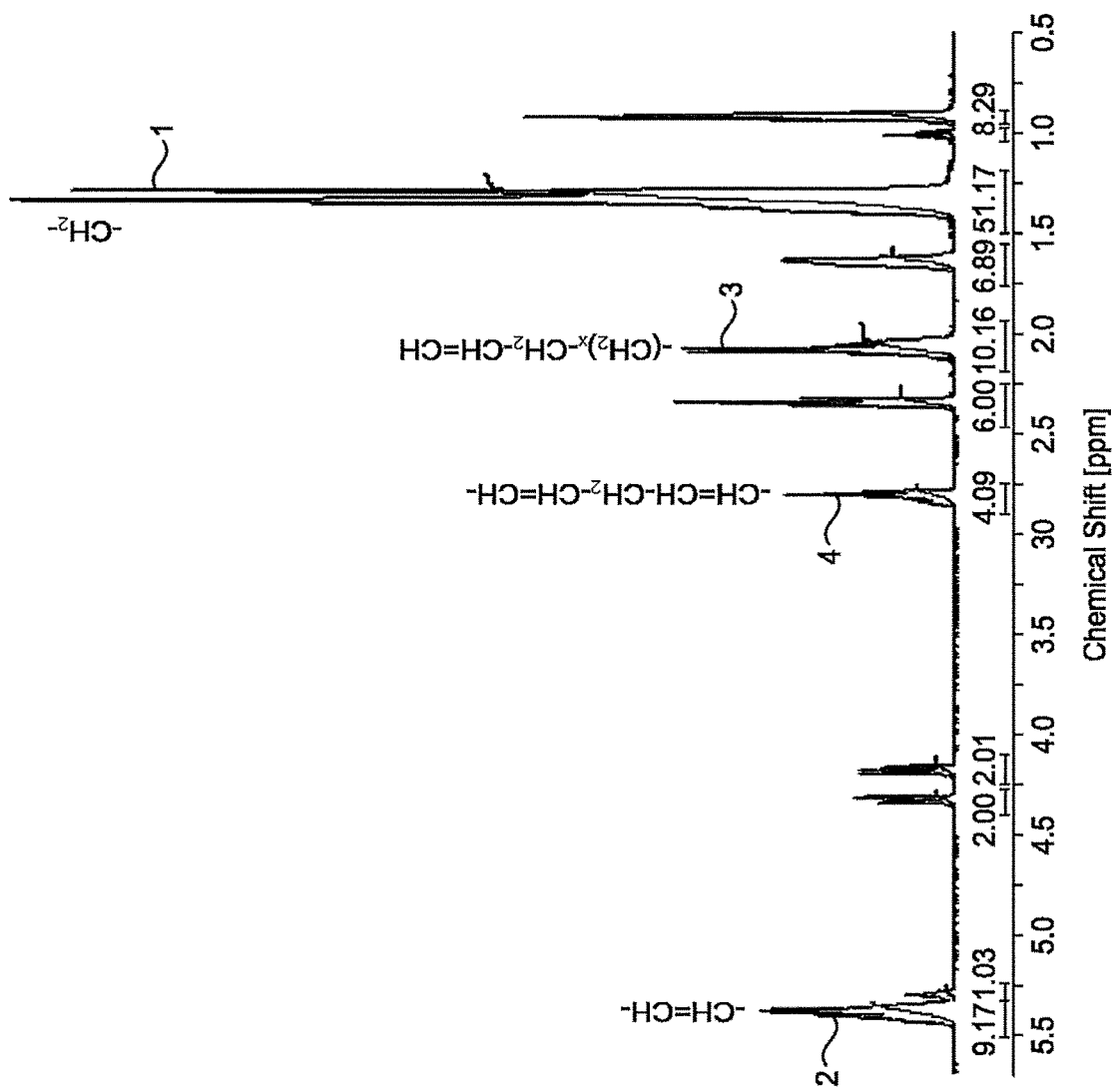
FIG. 2 is a chart for explaining a background related to the embodiment.

FIG. 2 is a chart for explaining the background of the embodiment and illustrates an example of an MRS spectrum while the horizontal axis expresses chemical shift values. Aliphatic protons 1 are protons corresponding to the structure —$CH_2$—$CH_2$— and have a chemical shift value of approximately 1.3 ppm. The aliphatic protons 1 are protons related to saturated fat and are the most common protons among protons structuring fat signals. Olefinic fat protons 2 are protons corresponding to the structure —CH=CH— and have a chemical shift value of approximately 5.3 ppm. Monounsaturated fat protons 3 are protons corresponding to the structure —CH=CH—$CH_2$—$(CH_2)_n$— and have a chemical shift value of approximately 2.0 ppm. Polyunsaturated fat protons 4 are protons corresponding to the structure —CH=CH—$CH_2$—CH=CH— and have a chemical shift value of approximately 2.8 ppm. The chemical shift value of water is approximately 4.7 ppm.

Generally speaking, when the amounts of CH—O(C=O)—, $CH_2$—O(C=O), and —O—(C=O)—$CH_2$ in triglyceride are assumed to be constant, the content amounts of fat protons vary from large to small in the following order: the aliphatic fat protons 1, the olefinic fat protons 2, the monounsaturated fat protons 3, and the polyunsaturated fat protons 4.

To quantify signals of saturated fat and unsaturated fat, Point Resolved Spectroscopy (PRESS) may be used, for example, by which an image taking process is performed by implementing single-voxel Magnetic Resonance Spectroscopy (MRS). However, it is desirable to quantify fats by using a two-dimensional (2D) or three-dimensional (3D) image, instead of the single-voxel image taking process. Further, when impacts of B0 non-uniformity or susceptibility effects are present, it may be difficult in some situations to realize high resolution with MRS.

Further, a Dixon-type imaging method is also known. According to the Dixon-type imaging method, an image taking process is performed twice by using a spin echo while slightly varying Echo Time (TE) values, for example, so that a signal of fat and a signal of water have the same phase as each other ("being in-phase") and have phases opposite to each other ("being out of phase").

In this situation, for example, when the signal intensity of an in-phase image is expressed as IP, while the signal intensity of water is expressed as W, and the signal intensity of fat is expressed as F, IP=W+F is satisfied. Further, for example, when the signal intensity of an image having an opposite phase is expressed as OP, OP=W−F is satisfied. When these two expressions are taken as simultaneous equations, W=½(IP+OP) and F=½(IP−OP) are satisfied. Accordingly, by simultaneously satisfying the equations with the pieces of data obtained from the image taking process performed twice, it is possible to separately extract the signal of water and the signal of the fat.

Further, examples of the Dixon-type imaging method include the Iterative Decomposition of water and fat with Echo Asymmetry and Least-squares estimation (IDEAL) method.

However, according to the IDEAL method, olefinic fat is not taken into consideration, for example. Further, the IDEAL method is a method for estimating the shape of a spectrum and is not a method for directly measuring the constituent elements of mutually-different types of fat.

The regular Dixon-type imaging method may not work in some situations, when no signal of water is present in a pixel.

In view of the background described above, the magnetic resonance imaging apparatus 100 according to an embodiment includes the sequence controlling circuitry 120 and the processing circuitry 150. The sequence controlling circuitry 120 is configured to acquire a first piece of data by executing a first pulse sequence having a first Echo Time (TE) value, to acquire a second piece of data by executing a second pulse sequence having a second TE value different from the first TE value, and to acquire a third piece of data by executing a third pulse sequence having a third TE value different from the first and the second TE values. The processing circuitry 150 extracts a signal related to water, a signal related to a first fat, and a signal related to a second fat, on the basis of the first piece of data, the second piece of data, and the third piece of data, by employing the calculating function 140.

In this situation, by employing the calculating function 140, the processing circuitry 150 quantifies the aliphatic fat protons 1, the olefinic fat protons 2, the polyunsaturated fat protons 4, and the monounsaturated fat protons 3, based on chemical shift values of constituent elements of each type of fat.

As a result, it is possible to quantify saturated and unsaturated fat signals, not in single-voxel MRS, but in a 2D- or 3D-image. Consequently, for example, it is possible to realize an imaging process on a tissue having fat constituent elements of multiple types.

In this situation, the sequence controlling circuitry 120 is also able to set a center frequency F0 to a frequency other than the frequency corresponding to the chemical shift of water, e.g., as a frequency corresponding to the chemical shift of the aliphatic protons 1. In that situation, the sequence controlling circuitry 120 may execute: a pulse sequence using such a TE value that causes a signal of the aliphatic protons 1 and a signal of the olefinic fat protons 2 to have phases opposite to each other; a pulse sequence using such a TE value that causes a signal of the aliphatic protons 1 and a signal of the unsaturated fat protons 3 to have phases opposite to each other; or a pulse sequence using such a TE value that causes a signal of the aliphatic protons 1 and a signal of the polyunsaturated fat protons 4 to have phases opposite to each other.

For example, with a fat tissue containing no water, it is possible to perform rendering processes effectively by selecting the center frequency in this manner.

This configuration will be explained, with reference to FIGS. 3 to 10.

Figure 3A:
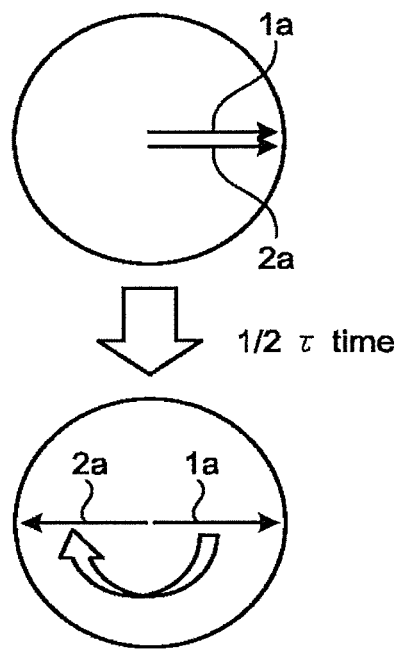
FIGS. 3A, 3B, and 3C are other charts for explaining the background of the embodiment.
Figure 3B:
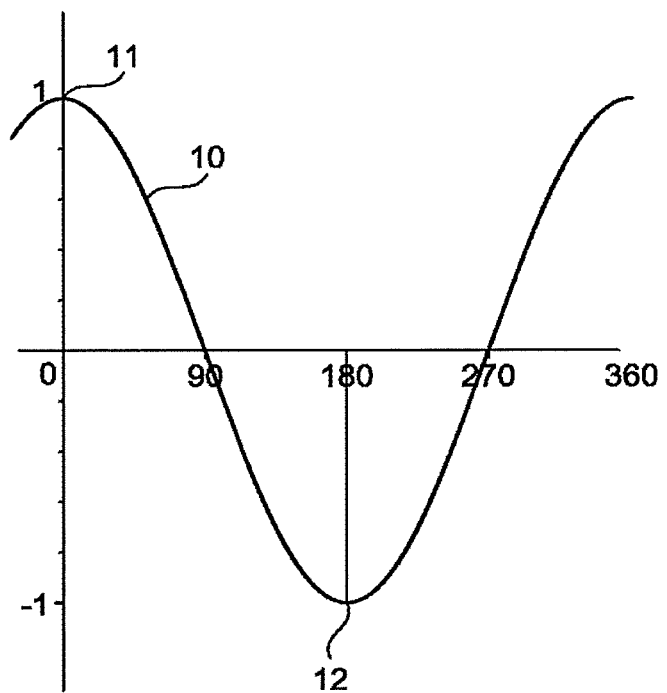
Figure 3C:
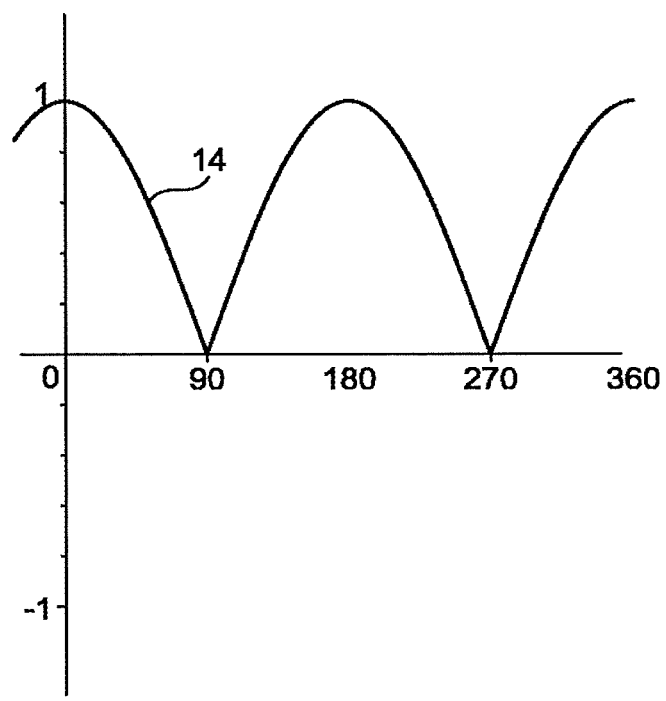

First, with reference to FIGS. 3A to 3C, a method for extracting a predetermined signal from data containing mutually-different types of signals will be explained. FIGS. 3A to 3C are charts for explaining a background of an embodiment.

The top section of FIG. 3A illustrates a signal 1a and a signal 2a different from the signal 1a, observed immediately after a 90-degree RF pulse is applied by the sequence controlling circuitry 120. The signal 1a may be a signal of water, for example. The signal 2a may be a signal of fat, for example. Immediately after the 90-degree RF pulse is applied, the phases of the signal 1a and the signal 2a are in-phase with each other.

The bottom section of FIG. 3A illustrates the signal 1a and the signal 2a observed when a time period $\frac{1}{2}\tau$ has elapsed since the time corresponding to the top section of FIG. 3A. As illustrated in the bottom section of FIG. 3A, when the time period $\frac{1}{2}\tau$ has elapsed since the signal 1a and the signal 2a became in-phase with each other, the signal 1a and the signal 2a come to have phases opposite to each other. Also, when a time period $\tau$ has elapsed since the signal 1a and the signal 2a became in-phase with each other, the signal 1a and the signal 2a become in-phase with each other again. In other words, the time period $\tau$ is the duration from the time when the signal 1a and the signal 2a become in-phase with each other, to the time when the two signals again become in-phase with each other. By arranging the time period $\tau$ to be a time length optimal for the target substance to be rendered, it is possible to obtain an appropriate image.

In this situation, the phase difference between the signal 1a and the signal 2a is in proportion to the difference between the chemical shift of the substance structuring the signal 1a and the chemical shift of the substance structuring the signal 2a, provided that the elapsed time period since the two signals become in-phase with each other is the same. The phase difference between the two signals is in proportion to the difference in the chemical shift between the substances structuring the two signals.

In FIG. 3B, a curve 10 indicates a relative value of the signal intensity of the signal 2a, while the horizontal axis expresses the phase of the signal 2a relative to the phase of the signal 1a. At a point 11, the signal 1a and the signal 2a are in-phase with each other. At a point 12, the signal 1a and the signal 2a have phases opposite to each other.

Further, in FIG. 3C, a curve 14 is obtained by expressing the curve 10 according to the intensity levels, i.e., absolute values of the signal.

As observed from FIGS. 3A to 3C, for example, by executing a pulse sequence in which the TE value is shifted by the time period $\frac{1}{2}\tau$ by shifting the application time of a 180-degree pulse, for example, the sequence controlling circuitry 120 is able to perform an image taking process with such timing that causes the signal 1a and the signal 2a to have phases opposite to each other. Further, by executing a pulse sequence in which the TE value is shifted by a predetermined time period, the sequence controlling circuitry 120 is able to perform image taking processes while shifting the phase of the signal 1a and the phase of the signal 2a.

In this situation, the magnetic resonance imaging apparatus 100 according to an embodiment is configured to separately extract a signal related to water and signals related to a plurality of types of fat. For example, by employing the calculating function 140, the processing circuitry 150 separately extracts the signal related to water, a signal related to a first fat, and a signal related to a second fat. In other words, during this process, there are at least three types of signals, and three unknown quantities are present. Accordingly, to separately extract the three signals, it is necessary to use three simultaneous equations. Consequently, to extract the signals related to the plurality of types of fat, the sequence controlling circuitry 120 executes three pulse sequences having mutually-different TE values, while slightly varying the TE value.

Next, a process performed by the magnetic resonance imaging apparatus 100 according to a first embodiment will be explained, with reference to FIGS. 4 and 5A to 5D.

FIG. 4 is a flowchart for explaining a process performed by the magnetic resonance imaging apparatus 100 according to embodiments. The flowchart in FIG. 4 is applicable to both the first and second embodiments.

At first, at steps S100, S110, and S120, the magnetic resonance imaging apparatus 100 according to the embodiments executes three pulse sequences having mutually-different TE values. In one example, the sequence controlling circuitry 120 applies pulse sequences for a normal spin echo as a first pulse sequence, a second pulse sequence, and a third pulse sequence applied at steps S100, S110, and S120. For example, as the pulse sequences for the spin echo, the sequence controlling circuitry 120 executes the pulse sequences in which a 90-degree RF pulse is at first applied and subsequently a 180-degree RF pulse is applied.

In the first embodiment, for example, as illustrated in FIGS. 5A to 5D, the sequence controlling circuitry 120 executes the three consequent pulse sequences, namely, the first pulse sequence, the second pulse sequence, and the third pulse sequence, in such a manner that the center frequency (a carrier frequency) is equal to a frequency corresponding to the chemical shift of water. FIGS. 5A, 5B, 5C, and 5D are drawings for explaining processes performed by the magnetic resonance imaging apparatus 100 according to the first embodiment.

Figure 5A:
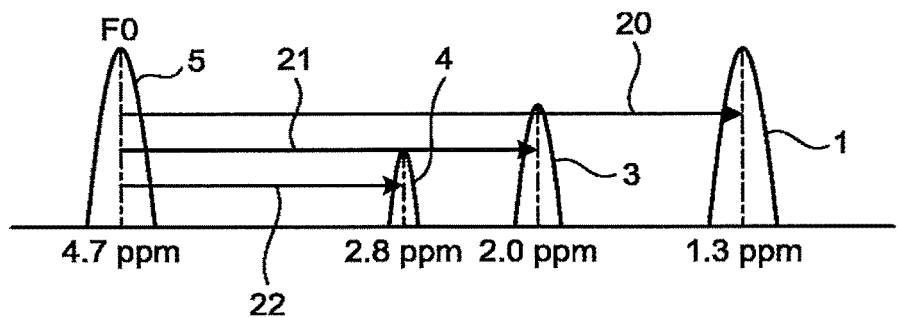
FIGS. 5A, 5B, 5C, and 5D are drawings for explaining processes performed by a magnetic resonance imaging apparatus according to a first embodiment.

As illustrated in FIG. 5A, the signal intensity of the aliphatic protons 1 is present in the position where the chemical shift is 1.3 ppm; the signal intensity of protons in water 5 is present in the position where the chemical shift is 4.7 ppm; the signal intensity of the monounsaturated fat protons 3 is present in the position where the chemical shift is 2.0 ppm; the signal intensity of the polyunsaturated fat protons 4 is present in the position where the chemical shift is 2.8 ppm. In the example in FIG. 5A, the sequence controlling circuitry 120 executes the three pulse sequences, namely, the first pulse sequence, the second pulse sequence, and the third pulse sequence in such a manner that the center frequency (the carrier frequency) in the pulse sequences is equal to the frequency corresponding to the chemical shift (4.7 ppm) of the protons in water.

At step S100 in FIG. 4, the sequence controlling circuitry 120 performs a first acquisition by which a first piece of data (hereinafter, simply "first data") is acquired by executing a first pulse sequence having a first TE value. For example, the sequence controlling circuitry 120 performs the first acquisition by which the first data is acquired by executing the first pulse sequence while using the first TE value that causes the signal of water and the signal related to the first fat to be in-phase with each other. In this situation, for example, the first pulse sequence is a pulse sequence for a spin echo, for example. Typically, the first pulse sequence is structured with, for example, an RF pulse of which the flip angle is 90 degrees and an RF pulse of which the flip angle is 180 degrees.

Figure 5B:
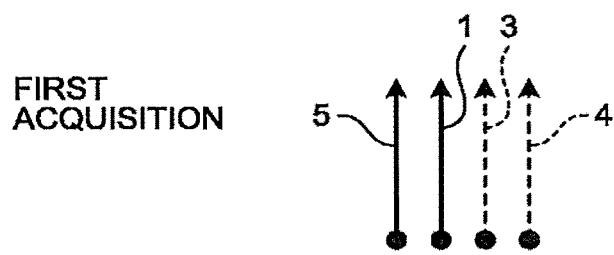

FIG. 5B illustrates an example of the first acquisition. As illustrated in FIG. 5B, the sequence controlling circuitry 120 performs the first acquisition by which the first data is acquired by executing the first pulse sequence while using the first TE value that causes the signal related to the protons in water 5 and the signal related to the aliphatic protons 1 to be in-phase with each other. In that situation, not only the signal related to the protons in water 5 and the signal related to the aliphatic protons 1, but also a signal related to the monounsaturated fat protons 3 and a signal related to the polyunsaturated fat protons 4 are also in-phase with each other.

Figure 5C:
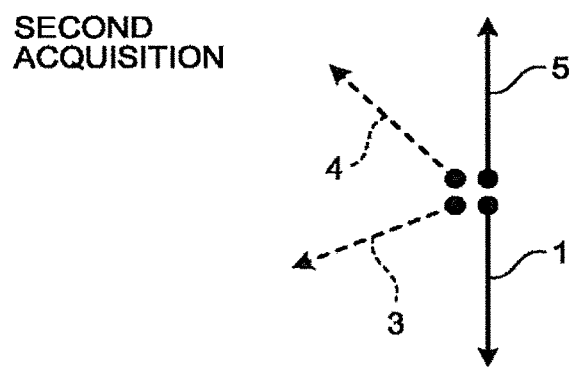

Further, at step S110 in FIG. 4, the sequence controlling circuitry 120 acquires a second piece of data (hereinafter, simply "second data") by executing a second pulse sequence having a second TE value different from the first TE value. For example, the sequence controlling circuitry 120 performs a second acquisition by which the second data is acquired by executing the second pulse sequence while using such a TE value that causes the signal related to water and the signal related to the first fat to be out of phase with each other, for example, that causes the two signals to have phases that are different from each other by 180 degrees and are opposite to each other. For example, as illustrated in FIG. 5C, the sequence controlling circuitry 120 performs the second acquisition by which the second data is acquired by executing the second pulse sequence while using such a TE value that causes the signal related to the protons in water 5 and the signal related to the aliphatic protons 1 to have phases opposite to each other. In this situation, for example, by shifting the application timing of the 180-degree pulse to be applied by the time period τ/2, the sequence controlling circuitry 120 performs the second acquisition by which the second data is acquired by executing the second pulse sequence while using such a TE value that causes the signal related to the protons in water 5 and the signal related to the aliphatic protons 1 to have phases opposite to each other. In that situation, for example, the phase of the signal related to the monounsaturated fat protons 3 and the polyunsaturated fat protons 4 are each different from the phase of the signal related to the protons in water 5.

Figure 5D:
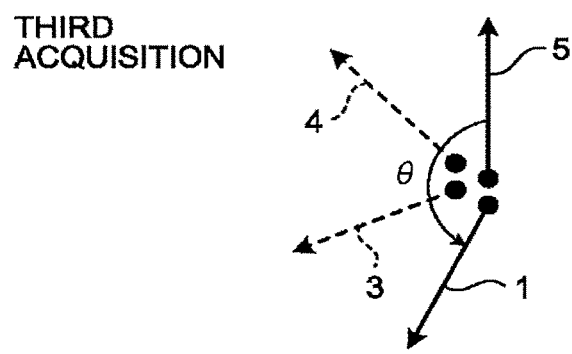

Subsequently, at step S120 in FIG. 4, the sequence controlling circuitry 120 acquires a third piece of data (hereinafter, simply "third data") by executing a third pulse sequence having a third TE value different from the first and the second TE values. For example, the sequence controlling circuitry 120 performs a third acquisition by which the third data is acquired by executing the third pulse sequence while using the third TE value that causes the signal related to water and the signal related to the first fat to be out of phase with each other. For example, as illustrated in FIG. 5D, the sequence controlling circuitry 120 performs the third acquisition by which the third data is acquired by executing the third pulse sequence while using such a TE value that causes the signal related to the protons in water 5 and the signal related to the aliphatic protons 1 to be out of phase with each other. In this situation, by shifting the application timing of the 180-degree pulse to be applied by a prescribed time period, for example, the sequence controlling circuitry 120 performs the third acquisition by which the third data is acquired by executing the third pulse sequence while using such a TE value that causes the signal related to the protons in water 5 and the signal related to the aliphatic protons 1 to be out of phase with each other. In that situation, for example, the phase of the signal related to the monounsaturated fat protons 3 and the phase of the signal related to the polyunsaturated fat protons 4 are each different from the phase of the signal related to the protons in water 5.

In this situation, in the first acquisition, when the signal related to the protons in water 5 is expressed as W, the signal related to the aliphatic protons 1 is expressed as A, the signal related to the monounsaturated fat protons 3 is expressed as M, and the signal related to the polyunsaturated fat protons 4 is expressed as P, the signal value obtained from the first acquisition is expressed as "W+A+M+P".

Further, the signal value obtained from the second acquisition is expressed as "W−A+aM+bP". In this situation, the coefficients a and b are predetermined coefficients that are each determined according to the phase of the monounsaturated fat protons 3 and the phase of the polyunsaturated fat protons 4 in the second acquisition. By employing the calculating function 140, the processing circuitry 150 calculates the coefficients a and b related to these signals and the like at step S130 (explained later).

Further, the signal value obtained from the third acquisition is expressed as "W+cA+dM+eP". In this situation, the coefficient c is a predetermined coefficient determined according to the phase of the aliphatic protons 1 in the third acquisition. Further, the coefficients d and e are predetermined coefficients determined according to the phase of the monounsaturated fat protons 3 and the phase of the polyunsaturated fat protons 4 in the third acquisition. By employing the calculating function 140, the processing circuitry 150 calculates the coefficients c, d, and e related to these signals, and the like, at step S130 (explained later).

Returning to the description of FIG. 4, at step S130, by employing the calculating function 140, the processing circuitry 150 calculates the coefficients related to the signals based on the values of the chemical shift of water, the chemical shift of the first fat, and the chemical shift of the second fat.

For instance, at first, an example will be explained in which only the signal W related to the protons in water 5, the signal A related to the aliphatic protons 1, and the signal M related to the monounsaturated fat protons 3 are taken into consideration. In that situation, the signal value obtained from the first acquisition is expressed as "W+A+M". Further, the signal value obtained from the second acquisition is expressed as "W−A+aM" by using the coefficient a. The signal value obtained from the third acquisition is expressed as "W+bA+cM" by using the coefficients b and c. By employing the calculating function 140, the processing circuitry 150 calculates the coefficients a, b, and c related to these signals, and the like.

In this situation, by employing the calculating function 140, the processing circuitry 150 calculates the coefficients related to the signals, by using the notion that the phase difference between the different types of protons is in proportion to the difference in the chemical shift between the different types of protons.

For example, as indicated by an arrow 20, the difference between the chemical shift of the protons in water 5 and the chemical shift of the aliphatic protons 1 is calculated as 4.7 ppm−1.3 ppm=3.4 ppm. Further, as indicated by an arrow 21, the difference between the chemical shift of the protons in water 5 and the chemical shift of the monounsaturated fat protons 3 is calculated as 4.7 ppm−2.0 ppm=2.7 ppm.

Further, as illustrated in FIG. 5C, in the second acquisition, because the protons in water 5 and the aliphatic protons 1 have phases opposite to each other, the phase difference therebetween is 180°. Accordingly, the phase difference between the protons in water 5 and the monounsaturated fat protons 3 is calculated as 180°×(2.7/3.4)=142°. Accordingly, by employing the calculating function 140, the processing circuitry 150 calculates the coefficient a related to the signal of the monounsaturated fat protons 3 in the second acquisition when the center frequency is selected to be the chemical shift of the protons in water 5 as cos(142°)=−0.798 by using the cosine of the phase difference between the protons in water 5 and the monounsaturated fat protons 3.

Similarly, as illustrated in FIG. 5D, in the third acquisition, the phase difference between the protons in water 5 and the aliphatic protons 1 is expressed as e.

Accordingly, in the third acquisition, the phase difference between the protons in water 5 and the monounsaturated fat protons 3 is calculated as $\theta \times (2.7/3.4)=0.794\theta$.

By using the cosine of the phase difference, the processing circuitry 150 calculates, by employing the calculating function 140, the coefficient b related to the signal of the aliphatic protons 1 in the third acquisition when the center frequency is selected to be the chemical shift of the protons in water 5 as cos θ.

Further, by using the cosine of the phase difference, the processing circuitry 150 calculates, by employing the calculating function 140, the coefficient c related to the signal of the monounsaturated fat protons 3 in the third acquisition when the center frequency is selected to be the chemical shift of the protons in water 5 as cos(0.794θ).

Next, an example will be explained in which only the signal W related to the protons in water 5, the signal A related to the aliphatic protons 1, and the signal P related to the polyunsaturated fat protons 4 are taken into consideration. In that situation, the signal value obtained from the first acquisition is expressed as "W+A+P". Further, the signal value obtained from the second acquisition is expressed as "W−A+aP" by using the coefficient a. The signal value obtained from the third acquisition is expressed as "W+bA+cP" by using the coefficients b and c. By employing the calculating function 140, the processing circuitry 150 calculates the coefficients a, b, and c related to these signals, and the like.

When the calculations are performed similarly, the difference between the chemical shift of the protons in water 5 and the chemical shift of the polyunsaturated fat protons 4 is 1.9 ppm, as indicated by an arrow 22. Accordingly, in the second acquisition, the phase difference between the protons in water 5 and the polyunsaturated fat protons 4 is calculated as 180°×(1.9/3.4)=100.59°. Accordingly, by employing the calculating function 140, the processing circuitry 150 calculates the coefficient a related to the signal of the polyunsaturated fat protons 4 in the second acquisition when the center frequency is selected to be the chemical shift of the protons in water 5 as cos(100.59°)=−0.184, by using the cosine of the phase difference between the protons in water 5 and the polyunsaturated fat protons 4.

Similarly, as illustrated in FIG. 5D, in the third acquisition, the phase difference between the protons in water 5 and the aliphatic protons 1 is expressed as θ.

Accordingly, in the third acquisition, the phase difference between the protons in water 5 and the polyunsaturated fat protons 4 is calculated as $\theta \times (1.9/3.4)=0.558\theta$.

By using the cosine of the phase difference, the processing circuitry 150 calculates, by employing the calculating function 140, the coefficient b related to the signal of the aliphatic protons 1 in the third acquisition when the center frequency is selected to be the chemical shift of the protons in water 5 as cos θ.

Further, by using the cosine of the phase difference, the processing circuitry 150 calculates, by employing the calculating function 140, the coefficient c related to the signal of the polyunsaturated fat protons 4 in the third acquisition when the center frequency is selected to be the chemical shift of the protons in water 5 as cos(0.558θ).

In an embodiment, it is also possible to take into consideration all the four signals, namely, the signal W related to the protons in water 5, the signal A related to the aliphatic protons 1, the signal M related to the monounsaturated fat protons 3, and the signal P related to the polyunsaturated fat protons 4. It should be noted however, in that situation, because there are four unknown quantities, it is necessary to perform the acquisition four times, in order to separately extract these signals.

Accordingly, in that situation, the sequence controlling circuitry 120 performs the acquisition four times in total and performs the same process as described above.

Subsequently, at step S140, by employing the calculating function 140, the processing circuitry 150 extracts the signal of water, the signal of the first fat, and the signal of second fat from the first data, the second data, and the third data acquired by the sequence controlling circuitry 120 at steps S100, S110, and S120, on the basis of the coefficients related to the signals calculated at step S130.

For example, when only the signal W related to the protons in water 5, the signal A related to the aliphatic protons 1, and the signal M related to the monounsaturated fat protons 3 are taken into consideration, the first data, i.e., a signal value X obtained from the first acquisition is expressed as "X=W+A+M". Further, the second data, i.e., a signal value Y obtained from the second acquisition is expressed as "Y=W−A+aM", by using the coefficient a explained above. Further, the third data, i.e., a signal value Z obtained from the third acquisition is expressed as "Z=W+bA+cM", by using the coefficients b and c explained above. In this situation, by employing the calculating function 140, the processing circuitry 150 has calculated the coefficients related to the signals at step S130. By the calculating function 140, the processing circuitry 150 solves the simultaneous equations on the basis of the signal values X, Y, and Z obtained from the pieces of data acquired by the sequence controlling circuitry 120 at steps S100, S110, and S120, and the values of the coefficients a, b, and c calculated at step S130 so as to extract the signal W related to the protons in water 5, the signal A related to the aliphatic protons 1, and the signal M related to the monounsaturated fat protons 3. In other words, the sequence controlling circuitry 120 extracts the signal W related to the protons in water 5, the signal A related to the aliphatic protons 1, and the signal M related to the monounsaturated fat protons 3 as the signal related to water, the signal related to the first fat, and the signal related to the second fat.

Similarly, when only the signal W related to the protons in water 5, the signal A related to the aliphatic protons 1, and the signal P related to the polyunsaturated fat protons 4 are taken into consideration, the sequence controlling circuitry 120 extracts the signal W related to the protons in water 5, the signal A related to the aliphatic protons 1, and the signal M related to the polyunsaturated fat protons 4, as the signal related to water, the signal related to the first fat, and the signal related to the second fat.

In this manner, by employing the calculating function 140, the processing circuitry 150 extracts the signal related to water, the signal related to the first fat, and the signal related to the second fat, on the basis of the first data acquired by the sequence controlling circuitry 120 at step S100, the second data acquired by the sequence controlling circuitry 120 at step S110, and the third data acquired by the sequence controlling circuitry 120 at step S120, and the values of the chemical shift of water, the chemical shift of the first fat, and the chemical shift of the second fat.

Further, based on the signal of the water, the signal of the first fat, and the signal of the second fat extracted from each of the pixels in the image, the processing circuitry 150 is configured to generate either a two-dimensional image or a three-dimensional image. In the first embodiment, because the pulse sequences executed by the sequence controlling circuitry 120 are not limited to single-voxel MRS, the sequence controlling circuitry 120 is able to generate either the two-dimensional image or the three-dimensional image, from the pieces of first, second, and third data acquired at steps S100, S110, and S120.

As explained above, the magnetic resonance imaging apparatus 100 according to the embodiment is able to extract the signals of the plurality of types of fat.

Second Embodiment

In the first embodiment, the example is explained in which the sequence controlling circuitry 120 executes the pulse sequence in such a manner that the center frequency is equal to the frequency corresponding to the chemical shift of water. In the second embodiment, an example will be explained in which the sequence controlling circuitry 120 executes a pulse sequence in such a manner that the center frequency is equal to a frequency other than the chemical shift of water, e.g., a frequency corresponding to the chemical shift of a fat, so as to execute the pulse sequence that causes the fat and water to have phases opposite to each other.

Fat tissues do not necessarily contain water. Accordingly, with respect to fat tissues containing no water, for example, the sequence controlling circuitry 120 is able to efficiently perform data acquisitions by arranging the center frequency to be equal to a frequency other than the chemical shift of water.

A signal extracting process performed by the magnetic resonance imaging apparatus 100 according to the second embodiment will be explained with reference to FIG. 4 again and FIGS. 6A and 6B.

In the second embodiment also, the magnetic resonance imaging apparatus 100 executes three pulse sequences having mutually-different TE values at steps S100, S110, and S120. In one example, the sequence controlling circuitry 120 applies pulse sequences for a normal spin echo as the first pulse sequence, the second pulse sequence, and the third pulse sequence applied at steps S100, S110, and S120. For example, as the pulse sequences for the spin echo, the sequence controlling circuitry 120 executes the pulse sequences in which a 90-degree RF pulse is at first applied and subsequently a 180-degree RF pulse is applied.

Figure 6A:
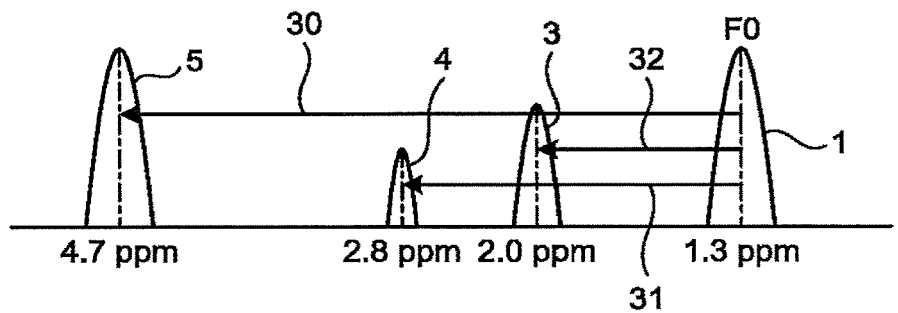
FIGS. 6A, 6B, 6C, and 6D are drawings for explaining processes performed by a magnetic resonance imaging apparatus according to a second embodiment.
Figure 6B:
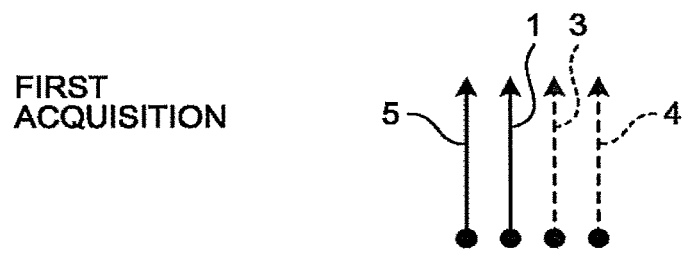

In the second embodiment, as illustrated in FIG. 6A, the sequence controlling circuitry 120 executes the first pulse sequence at step S100, the second pulse sequence at step S110, and the third pulse sequence at step S120, in such a manner that the center frequency (the carrier frequency) is equal to a frequency corresponding to the chemical shift of a fat. In the examples illustrated in FIGS. 6A to 6D, the sequence controlling circuitry 120 executes these pulse sequences in such a manner that the center frequency is equal to a frequency corresponding to the chemical shift of aliphatic fat.

At step S100, the sequence controlling circuitry 120 performs the first acquisition by which the first data is acquired by executing the first pulse sequence while using the first TE value that causes a signal of water and a signal related to the first fat to be in-phase with each other. As illustrated in FIG. 6B, similarly to the first embodiment, the sequence controlling circuitry 120 performs the first acquisition by which the first data is acquired by executing the first pulse sequence while using the first TE value that causes the signal related to the aliphatic protons 1 and the signal related to the protons in water 5 to be in-phase with each other.

Figure 6C:
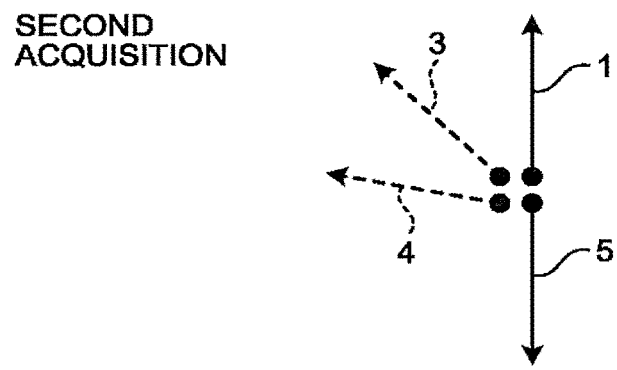

Subsequently, at step S110, the sequence controlling circuitry 120 performs the second acquisition by which the second data is acquired by executing the second pulse sequence by using such a TE value that causes the signal related to water and the signal related to the first fat to be out of phase with each other, for example, that causes the two signals to have phases that are different from each other by 180 degrees and are opposite to each other. For example, as illustrated in FIG. 6C, the sequence controlling circuitry 120 performs the second acquisition by which the second data is acquired by executing the second pulse sequence while using such a TE value that causes the signal related to the aliphatic protons 1 and the signal related to the protons in water 5 to have phases opposite to each other.

Figure 6D:
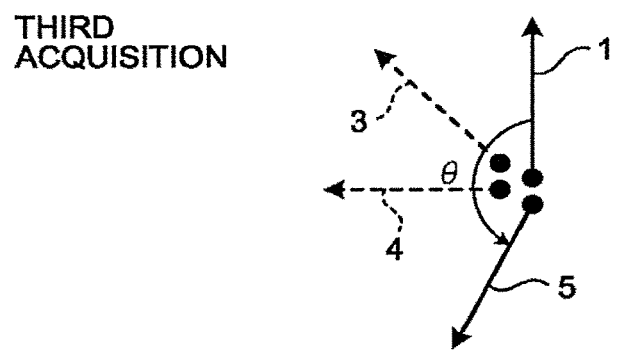

Subsequently, at step S120, the sequence controlling circuitry 120 performs the third acquisition by which the third data is acquired by executing the third pulse sequence while using the third TE value that causes the signal related to water and the signal related to the first fat to be out of phase with each other. For example, as illustrated in FIG. 6D, the sequence controlling circuitry 120 performs the second acquisition by which the third data is acquired by executing the third pulse sequence while using such a TE value that causes the signal related to the aliphatic protons 1 and the signal related to the protons in water 5 to be out of phase with each other.

At step S130, by employing the calculating function 140, the processing circuitry 150 calculates the coefficients related to the signals, based on the values of the chemical shift of water, the chemical shift of the first fat, and the chemical shift of the second fat.

Similar to the first embodiment, at first, an example will be explained in which only the signal W related to the protons in water 5, the signal A related to the aliphatic protons 1, and the signal M related to the monounsaturated fat protons 3 are taken into consideration. In that situation, the signal value obtained from the first acquisition is expressed as "A+W+M". Further, the signal value obtained from the second acquisition is expressed as "A−W+aM" by using the coefficient a. The signal value obtained from the third acquisition is expressed as "A+bW+cM" by using the coefficients b and c. By employing the calculating function 140, the processing circuitry 150 calculates the coefficients a, b, and c related to these signals, and the like.

Similar to the first embodiment, by employing the calculating function 140, the processing circuitry 150 calculates the coefficients related to the signals, by using the notion that the phase difference between the different types of protons is in proportion to the difference in the chemical shift between the different types of protons.

As indicated by an arrow 30, the difference between the chemical shift of the protons in water 5 and the chemical shift of the aliphatic protons 1 is calculated as 3.4 ppm. Further, as indicated by an arrow 32, the difference between the chemical shift of the aliphatic protons 1 and the chemical shift of the monounsaturated fat protons 3 is calculated as 0.7 ppm.

Further, as illustrated in FIG. 6C, in the second acquisition, because the protons in water 5 and the aliphatic protons 1 have phases opposite to each other, the phase difference therebetween is 180°. As a result, the phase difference between the aliphatic protons 1 and the monounsaturated fat protons 3 is calculated as 180°×(0.7/3.4)=37°. Accordingly, by employing the calculating function 140, the processing circuitry 150 calculates the coefficient a related to the signal of the monounsaturated fat protons 3 in the second acquisition when the center frequency is selected to be the chemical shift of the aliphatic protons 1 as cos(37°)=0.798 by using the cosine of the phase difference between the aliphatic protons 1 and the monounsaturated fat protons 3.

Further, in the third acquisition also, by employing the calculating function 140 and performing the same calculations as those in the first embodiment, the processing circuitry 150 calculates the coefficients related to the signals.

Next, an example will be explained in which only the signal W related to the protons in water 5, the signal A related to the aliphatic protons 1, and the signal P related to the polyunsaturated fat protons 4 are taken into consideration. In that situation, the signal value obtained from the first acquisition is expressed as "A+W+P". Further, the signal value obtained from the second acquisition is expressed as "A−W+aP" by using the coefficient a. The signal value obtained from the third acquisition is expressed as "A+bW+cP" by using the coefficients b and c. By employing the calculating function 140, the processing circuitry 150 calculates the coefficients a, b, and c related to these signals, and the like.

When the calculations are performed similarly, the difference between the chemical shift of the aliphatic protons 1 and the chemical shift of the polyunsaturated fat protons 4 is 1.5 ppm, as indicated by an arrow 31. As a result, in the second acquisition, the phase difference between the aliphatic protons 1 and the polyunsaturated fat protons 4 is calculated as 180°×(1.5/3.4)=79.4°. Accordingly, by employing the calculating function 140, the processing circuitry 150 calculates the coefficient a related to the signal of the polyunsaturated fat protons 4 in the second acquisition when the center frequency is selected to be the chemical shift of the aliphatic protons 1 as cos(79.4°)=0.184, by using the cosine of the phase difference between the aliphatic protons 1 and the polyunsaturated fat protons 4.

By employing the calculating function 140, the processing circuitry 150 also performs similar calculations with respect to the other coefficients.

Subsequently, at step S140, by employing the calculating function 140, the processing circuitry 150 extracts the signal of water, the signal of the first fat, and the signal of second fat from the first data, the second data, and the third data acquired by the sequence controlling circuitry 120 at steps S100, S110, and S120, on the basis of the coefficients related to the signals calculated at step S130.

Third Embodiment

In the first embodiment, the sequence controlling circuitry 120 executes the pulse sequence in such a manner that the center frequency is equal to the frequency corresponding to the chemical shift of the protons in water 5 and executes the pulse sequence that causes the signal of the aliphatic protons 1 and the signal of the protons in water 5 to be in-phase with each other and the pulse sequence that causes the signal of the aliphatic protons 1 and the signal of the protons in water 5 to have the phases opposite to each other.

Further, in the second embodiment, the sequence controlling circuitry 120 executes the pulse sequence in such a manner that the center frequency is equal to the frequency corresponding to the chemical shift of the aliphatic protons 1 and executes the pulse sequence that causes the signal of the aliphatic protons 1 and the signal of the protons in water 5 to be in-phase with each other and the pulse sequence that causes the signal of the aliphatic protons 1 and the signal of the protons in water 5 to have phases opposite to each other.

In a third embodiment, the sequence controlling circuitry 120 performs a pulse sequence in such a manner that the center frequency is equal to a frequency corresponding to the chemical shift of the signal of the first fat and executes a pulse sequence that causes the signal of the first fat and the signal of the second fat to be in-phase with each other and a pulse sequence that causes the signal of the first fat and the signal of the second fat to be out of phase with each other, i.e., to have phases opposite to each other, for example.

There are some fat tissues that contain no water. Accordingly, with those fat tissues, the pulse sequences described above are effective.

For example, the first fat may be aliphatic fat, whereas the second fat is olefinic fat. This example is illustrated in FIG. 7. FIG. 7 is a chart for explaining a process performed by the magnetic resonance imaging apparatus 100 according to the third embodiment.

The upper section of FIG. 7 illustrates an example in which the sequence controlling circuitry 120 performs an acquisition in which the signal of a first fat and the signal of a second fat become in-phase with each other. The sequence controlling circuitry 120 executes a pulse sequence that causes the center frequency to be equal to the frequency of the signal of the aliphatic protons 1 serving as the first fat. In that situation, the sequence controlling circuitry 120 executes a first pulse sequence by using a first TE value that causes the signal of the aliphatic protons 1 serving as the signal related to the first fat and the signal of the olefinic fat protons 2 serving as the signal related to the second fat to be in-phase with each other (called aoip: aliphatic-olefinic in-phase).

Further, the bottom section of FIG. 7 illustrates an example in which the sequence controlling circuitry 120 performs an acquisition that causes the signal of the first fat and the signal of the second fat to be out of phase with each other, for example, that causes the signal of the first fat and the signal of the second fat to have phases opposite to each other. The sequence controlling circuitry 120 executes a pulse sequence that causes the center frequency to be equal to the frequency of the signal of the aliphatic protons 1 serving as the first fat. In that situation, the sequence controlling circuitry 120 executes a second pulse sequence by using a second TE value that causes the signal of the aliphatic protons 1 serving as the signal related to the first fat and the signal of the olefinic fat protons 2 serving as the signal related to the second fat to be out of phase with each other, e.g., that causes the two signals to have phases opposite to each other (called aoop: aliphatic-olefinic out-of-phase).

When the signal of the aliphatic protons 1 and the signal of the olefinic fat protons 2 are acquired while having the phases opposite to each other, the phase of the olefinic fat protons 2 is inverted from the phase thereof observed when the signal of the aliphatic protons 1 and the signal of the olefinic fat protons 2 are acquired while being in-phase with each other. Further, when the signal of the aliphatic protons 1 and the signal of the olefinic fat protons 2 are acquired while having the phases opposite to each other, because the signal of the aliphatic protons 1 and the signal of the olefinic fat protons 2 are mixed with each other, the signal intensity is exhibited near the frequency of the aliphatic protons 1, which is the center frequency, as indicated by a spectrum 2X.

In the situation illustrated in FIG. 7, when the imaged target contains no water, because the signal of the protons in water 5 is absent, it is possible to separate the signal of the aliphatic protons 1 serving as the first fat and the signal of the olefinic fat protons 2 serving as the second fat, by performing the acquisition only twice.

When the imaged target contains water, the sequence controlling circuitry 120 executes the third pulse sequence by using the third TE value that causes the signal of the first fat and the signal of the second fat to be out of phase with each other.

A signal extracting process performed by the magnetic resonance imaging apparatus 100 according to the third embodiment will be explained, with reference to FIGS. 4 and 8A to 8D.

In the third embodiment also, at steps S100, S110, and S120, the magnetic resonance imaging apparatus 100 executes three pulse sequences having mutually-different TE values. In one example, the sequence controlling circuitry 120 applies pulse sequences for a normal spin echo as the first pulse sequence, the second pulse sequence, and the third pulse sequence applied at steps S100, S110, and S120. For example, as the pulse sequences for the spin echo, the sequence controlling circuitry 120 executes the pulse sequences in which a 90-degree RF pulse is at first applied and subsequently a 180-degree RF pulse is applied.

Figure 8A:
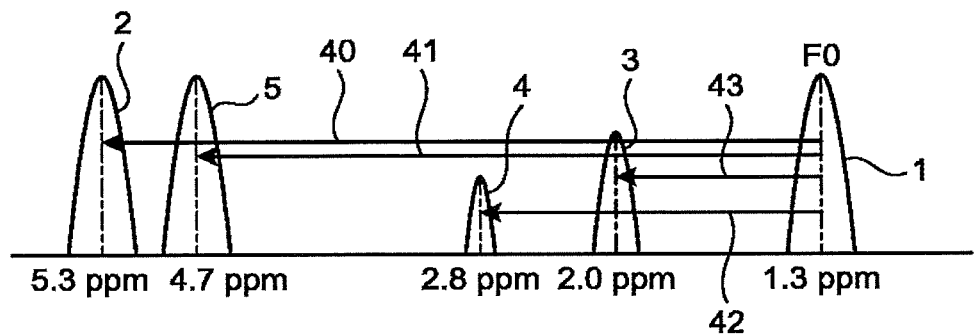
Figure 8B:
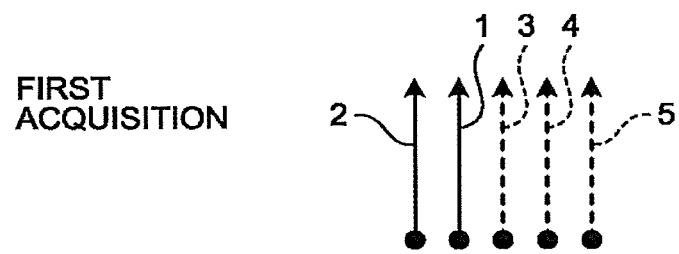

In the third embodiment, as illustrated in FIG. 8A, the sequence controlling circuitry 120 executes, similarly to the second embodiment, the first pulse sequence at step S100, the second pulse sequence at step S110, and the third pulse sequence at step S120, in such a manner that the center frequency (the carrier frequency) is equal to a frequency corresponding to the chemical shift of a fat. In the examples in FIGS. 8A to 8D, the sequence controlling circuitry 120 executes these pulse sequences in such a manner that the center frequency is equal to the frequency corresponding to the chemical shift of aliphatic fat.

At step S100, the sequence controlling circuitry 120 executes the first pulse sequence by using the first TE value that causes the signal of the aliphatic protons 1 serving as the first fat and the signal of the olefinic fat protons 2 serving as the second fat to be in-phase with each other.

Subsequently, at step S110, the sequence controlling circuitry 120 performs the second acquisition by which the second data is acquired by executing the second pulse sequence while using such a TE value that causes the signal of the aliphatic protons 1 serving as the first fat and the signal of the olefinic fat protons 2 serving as the second fat to be out of phase with each other, for example, that causes the two signals to have phases that are different from each other by 180 degrees and are opposite to each other.

Figure 8C:
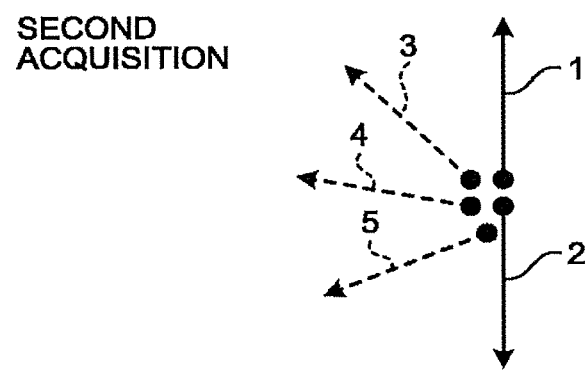

For example, as illustrated in FIG. 8C, the sequence controlling circuitry 120 performs the second acquisition by which the second data is acquired by executing the second pulse sequence while using such a TE value that causes the signal related to the aliphatic protons 1 and the signal related to olefinic fat protons 2 to have phases opposite to each other.

Figure 8D:
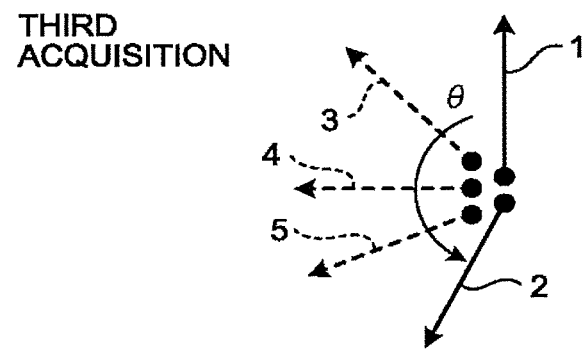

Subsequently, at step S120, the sequence controlling circuitry 120 performs the third acquisition by which the third data is acquired by executing the third pulse sequence while using the third TE value that causes the signal of the aliphatic protons 1 serving as the first fat and the signal of the olefinic fat protons 2 serving as the second fat to be out of phase with each other. For example, as illustrated in FIG. 8D, the sequence controlling circuitry 120 performs the third acquisition by which the third data is acquired by executing the third pulse sequence while using such a TE value that causes the signal of the aliphatic protons 1 serving as the first fat and the signal of the olefinic fat protons 2 serving as the second fat to be out of phase with each other.

At step S130, by employing the calculating function 140, the processing circuitry 150 calculates the coefficients related to the signals on the basis of the values of the chemical shift of the first fat, the chemical shift of the second fat, and the chemical shift of the substance for which the coefficients are calculated.

First, an example will be explained in which the only the signal W related to the protons in water 5, the signal A related to the aliphatic protons 1, and a signal O related to olefinic fat protons 2 are taken into consideration. In that situation, the signal value obtained from the first acquisition is expressed as "A+O+W". Further, the signal value obtained from the second acquisition is expressed as "A−O+aW" by using the coefficient a. Further, the signal value obtained from the third acquisition is expressed as "A+bO+cW" by using the coefficients b and c. By employing the calculating function 140, the processing circuitry 150 calculates the coefficients a, b, and c related to these signals, and the like.

Similarly to any of the embodiments described above, by employing the calculating function 140, the processing circuitry 150 calculates the coefficients related to the signals by using the notion that the phase difference between the different types of protons is in proportion to the difference in the chemical shift between the different types of protons.

As indicated by an arrow 40, the difference between the chemical shift of the aliphatic protons 1 and the chemical shift of the olefinic fat protons 2 is 4.0 ppm. Further, as indicated by an arrow 41, the difference between the chemical shift of the protons in water 5 and the chemical shift of aliphatic protons 1 is 3.4 ppm. Further, as indicated by an arrow 42, the difference between the chemical shift of the polyunsaturated fat protons 4 and the chemical shift of aliphatic protons 1 is 1.5 ppm. Further, as indicated by an arrow 43, the difference between the chemical shift of the monounsaturated fat protons 3 and the chemical shift of the aliphatic protons 1 is 0.7 ppm.

Further, as illustrated in FIG. 8C, in the second acquisition, because the olefinic fat protons 2 and the aliphatic protons 1 have phases opposite to each other, the phase difference is 180°. Accordingly, the phase difference between the protons in water 5 and the aliphatic protons 1 is calculated as 180°×(3.4/4.0)=153°. Consequently, by employing the calculating function 140, the processing circuitry 150 calculates the coefficient related to the signal of the protons in water 5 in the second acquisition when the center frequency is selected to be the chemical shift of the aliphatic protons 1 as cos(153°)=−0.891, by using the cosine of the phase difference between the olefinic fat protons 2 and the aliphatic protons 1.

Further, in the second acquisition, the phase difference between the polyunsaturated fat protons 4 and the aliphatic protons 1 is calculated as 180°×(1.5/4.0)=67.5°. Accordingly, by employing the calculating function 140, the processing circuitry 150 calculates the coefficient related to the signal of the polyunsaturated fat protons 4 in the second acquisition when the center frequency is selected to be the chemical shift of the aliphatic protons 1 as cos(67.5°)=0.383 by using the cosine of the phase difference between the polyunsaturated fat protons 4 and the aliphatic protons 1.

Further, in the second acquisition, the phase difference between the monounsaturated fat protons 3 and the aliphatic protons 1 is calculated as 180°×(0.7/4.0)=31.5°. Accordingly, by employing the calculating function 140, the processing circuitry 150 calculates the coefficient related to the signal of the monounsaturated fat protons 3 in the second acquisition when the center frequency is selected to be the chemical shift of the aliphatic protons 1 as cos(31.5°)=0.853 by using the cosine of the phase difference between the monounsaturated fat protons 3 and the aliphatic protons 1.

Further, also in the third acquisition, by performing the same calculations as those in the first embodiment, the processing circuitry 150 calculates the coefficients related to the signals by employing the calculating function 140.

Subsequently, at step S140, by employing the calculating function 140, the processing circuitry 150 extracts the signal of water, the signal of the first fat, and the signal of the second fat from the first data, the second data, and the third data acquired by the sequence controlling circuitry 120 at steps S100, S110, and S120, on the basis of the coefficients related to the signals calculated at step S130.

With reference to FIGS. 8A to 8D, the example is explained in which the sequence controlling circuitry 120 arranges the center frequency to be equal to the frequency of the aliphatic protons 1, and in the second acquisition, executes the pulse sequence that causes the signal of the olefinic fat protons 2 and the signal of the aliphatic protons 1 to have the phases opposite to each other; however, possible embodiments are not limited to this example.

In one example, as illustrated in FIG. 9, the sequence controlling circuitry 120 may arrange the center frequency to be equal to the frequency of the aliphatic protons 1 and, in the first acquisition illustrated in the top section of FIG. 9, may execute a pulse sequence that causes the signal of the polyunsaturated fat protons 4 and the signal of the aliphatic protons 1 to be in-phase with each other (called apip: aliphatic-polyunsaturated in-phase) and in the second acquisition illustrated in the bottom section of FIG. 9, may execute a pulse sequence that causes the signal of the polyunsaturated fat protons 4 and the signal of the aliphatic protons 1 to have phases opposite to each other (called apop: aliphatic-polyunsaturated out-of-phase).

When the signal of the aliphatic protons 1 and the signal of the polyunsaturated fat protons 4 are acquired while having the phases opposite to each other, the phase of the polyunsaturated fat protons 4 is inverted from the phase thereof observed when the signal of the aliphatic protons 1 and the signal of the polyunsaturated fat protons 4 are acquired while being in-phase with each other. Further, when the signal of the aliphatic protons 1 and the signal of the polyunsaturated fat protons 4 are acquired while having the phases opposite to each other, because the signal of the aliphatic protons 1 and the signal of the polyunsaturated fat protons 4 are mixed with each other, the signal intensity is exhibited near the frequency of the aliphatic protons 1, which is the center frequency, as indicated by a spectrum 4X.

Figure 10:
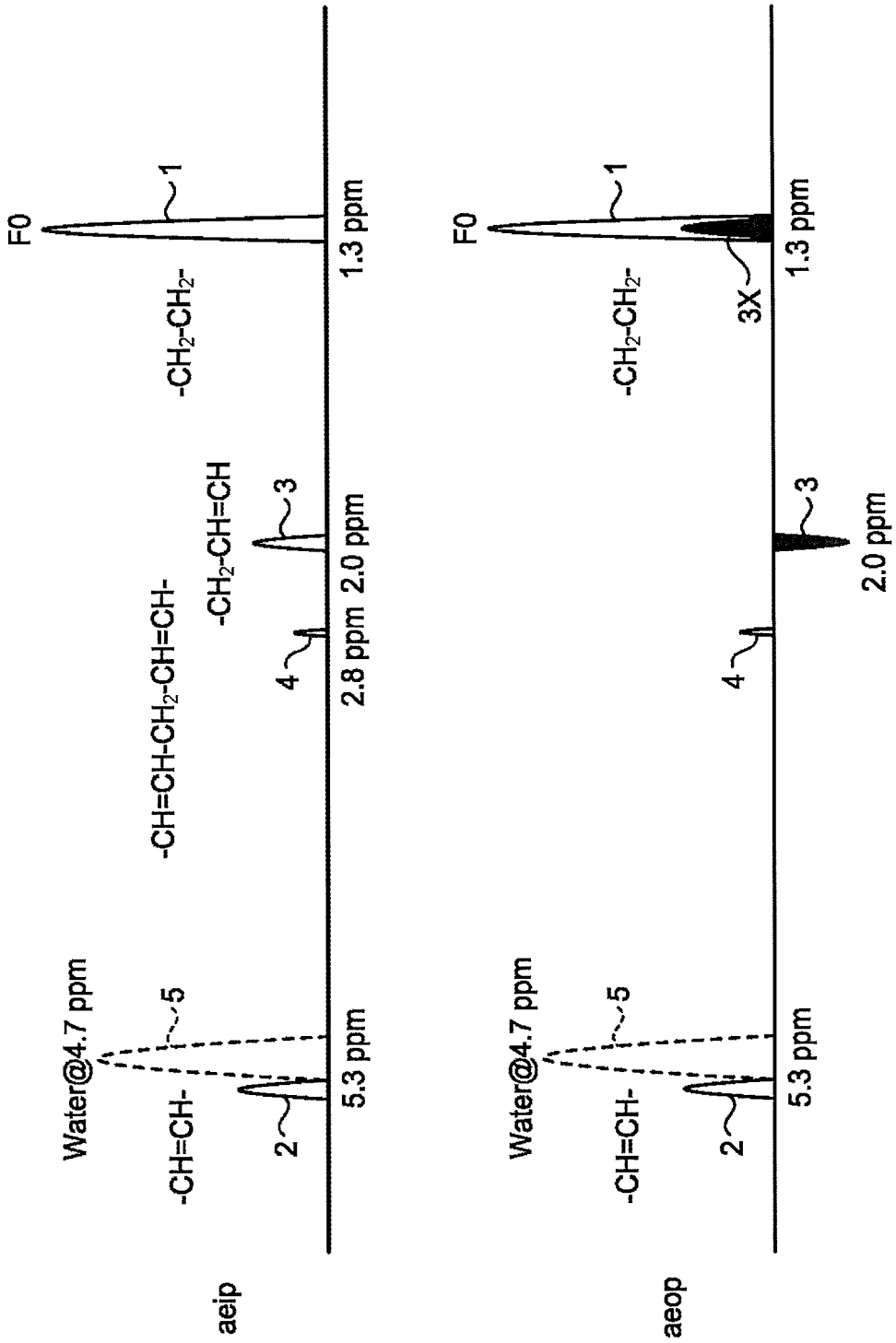

Further, in an example, as illustrated in FIG. 10, the sequence controlling circuitry 120 may arrange the center frequency to be equal to the frequency of the aliphatic protons 1 and, in the first acquisition illustrated in the top section of FIG. 10, may execute a pulse sequence that causes the signal of the monounsaturated fat protons 3 and the signal of the aliphatic protons 1 to be in-phase with each other (called aeip: aliphatic-monounsaturated in-phase), and in the second acquisition illustrated in the bottom section of FIG. 10, may execute a pulse sequence that causes the signal of the monounsaturated fat protons 3 and the signal of the aliphatic protons 1 to have phases opposite to each other (called aeop: aliphatic-monounsaturated out-of-phase).

When the signal of the aliphatic protons 1 and the signal of the monounsaturated fat protons 3 are acquired while having the phases opposite to each other, the phase of the monounsaturated fat protons 3 is inverted from the phase thereof observed when the signal of the aliphatic protons 1 and the signal of the monounsaturated fat protons 3 are acquired while being in-phase with each other. Further, when the signal of the aliphatic protons 1 and the signal of the monounsaturated fat protons 3 are acquired while having the phases opposite to each other, because the signal of the aliphatic protons 1 and the signal of the monounsaturated fat protons 3 are mixed with each other, the signal intensity is exhibited near the frequency of the aliphatic protons 1, which is the center frequency, as indicated by a spectrum 3X.

Figure 11:
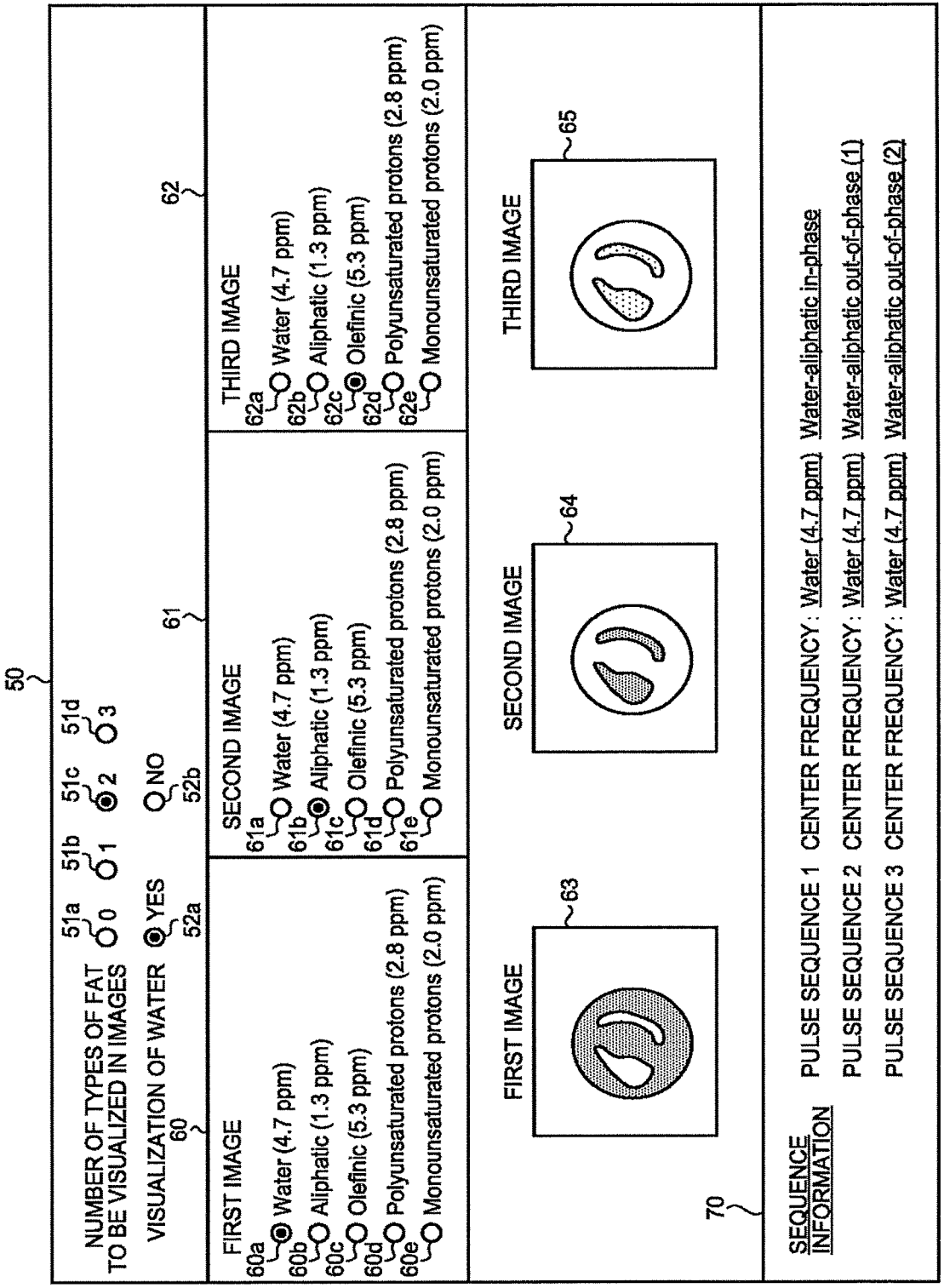
FIG. 11 illustrates an example of a Graphical User Interface (GUI) included in a magnetic resonance imaging apparatus according to an embodiment.

A GUI according to an embodiment A Graphical User Interface (GUI) included in the magnetic resonance imaging apparatus 100 according to an embodiment will be explained with reference to FIG. 11. FIG. 11 illustrates an example of the GUI included in the magnetic resonance imaging apparatus according to the embodiment.

An input panel 50 is a panel used by the processing circuitry 150, while employing the controlling function 133, to receive inputs from a user about the number of types of fat to be visualized in images and whether it is necessary to visualize water in an image. For example, by employing the controlling function 133, the processing circuitry 150 receives, from the user, the input about the number of types of fat to be visualized in images, via buttons 51a, 51b, 51c, and 51d, or the like. Further, by employing the controlling function 133, the processing circuitry 150 receives, from the user, the input about whether it is necessary to visualize water in an image via buttons 52a and 52b.

Subsequently, by employing the controlling function 133, the processing circuitry 150 calculates the number of pulse sequences to be executed by the sequence controlling circuitry 120, based on the input results received from the user via the buttons 51a, 51b, 51c, and 51d.

For example, when the number of types of fat to be visualized in images is "2", and it is necessary ("YES") to visualize water in an image, the number of images to be separately extracted is three. Accordingly, by employing the controlling function 133, the processing circuitry 150 calculates the number of pulse sequences to be executed by the sequence controlling circuitry 120 as "3". In another example, when the number of types of fat to be visualized in images is "3", and it is necessary ("YES") to visualize water in an image, the number of images to be separately extracted is four. Accordingly, by employing the controlling function 133, the processing circuitry 150 calculates the number of pulse sequences to be executed by the sequence controlling circuitry 120 as "4".

Input panels 60, 61 and 62 are panels used by the processing circuitry 150, while employing the controlling function 133, to receive inputs from the user about the targets to be visualized in images. For example, by employing the controlling function 133, the processing circuitry 150 receives a selection about the input of a substance to be rendered in a first image being displayed, via a button 60a, 60b, 60c, 60d, or 60e in the input panel 60. Similarly, by employing the controlling function 133, the processing circuitry 150 receives a selection about the input of a substance to be rendered in a second image being displayed, via a button 61a, 61b, 61c, 61d, or 61e in the input panel 61 and receives a selection about the input of a substance to be rendered in a third image being displayed, via a button 62a, 62b, 62c, 62d, or 62e in the input panel 62.

In this manner, by employing the controlling function 133, the processing circuitry 150 receives, from the user, the inputs about the first fat and the second fat to be rendered, through the input device 134, for example, via the aforementioned input panels 50, 60, 61, 62, and so on.

Subsequently, by employing the controlling function 133, the processing circuitry 150 establishes settings related to the first pulse sequence, the second pulse sequence, the third pulse sequence, and the like to be executed by the sequence controlling circuitry 120, based on the received input results. For example, by employing the controlling function 133, the processing circuitry 150 establishes, based on the received input results, the settings indicating the center frequency in the pulse sequence to be executed by the sequence controlling circuitry 120 and which signals are to be arranged to have phases opposite to each other by the executed pulse sequences. For example, when having received an input result indicating that "Water (4.7 ppm)" is to be rendered, the processing circuitry 150 sets, by employing the controlling function 133 and based on the received input result, the center frequency in the pulse sequence to be executed by the sequence controlling circuitry 120 to be "Water (4.7 ppm)". In contrast, when having received no input result indicating that "Water (4.7 ppm)" is to be rendered, the processing circuitry 150 sets, by employing the controlling function 133, the center frequency in the pulse sequence to be executed by the sequence controlling circuitry 120 to be "Aliphatic (1.3 ppm)".

Further, in an example, by employing the controlling function 133, the processing circuitry 150 determines to execute such a pulse sequence that causes a signal related to the target received as the target to be rendered in the first image and a signal related to the target received as the target to be rendered in the second image to have phases opposite to each other. For example, when an input result received from the user indicates that the first image is "Aliphatic (1.3 ppm)" and the second image is "Olefinic (5.3 ppm)", the processing circuitry 150 arranges, by employing the controlling function 133, the sequence controlling circuitry 120 to execute multiple pulse sequences having the center frequency set to "Aliphatic (1.3 ppm)" and including such pulse sequences that cause a signal related to Aliphatic (1.3 ppm) and a signal related to Olefinic (5.3 ppm) to be in-phase with each other and to have phases opposite to each other.

Further, by employing the controlling function 133, the processing circuitry 150 displays, for the user, information about the calculated settings related to the pulse sequences via a display panel 70.

After that, on the basis of the information about the settings related to the pulse sequences calculated by the processing circuitry 150, the sequence controlling circuitry 120 executes the first pulse sequence, the second pulse sequence, the third pulse sequence, and the like, while maintaining a receiver gain at the same level, i.e., while maintaining the setting conditions so that a piece of data obtained from each of the pulse sequences is able to properly serve as a target of a comparison. In other words, the sequence controlling circuitry 120 executes the first pulse sequence, the second pulse sequence and the third pulse sequence as a linked one acquisition while maintaining the receiver gain at the same level.

On the basis of the data obtained from the pulse sequences executed by the sequence controlling circuitry 120, the processing circuitry 150 performs the signal extracting process described above by employing the calculating function 140, generates images on the basis of the extracted signals, and causes display panels 63, 64, and 65, or the like, for example, to display the generated images.

In this manner, the processing circuitry 150 receives, from the user, the inputs about the plurality of types of fat including the inputs about the types of the first fat and the second fat, through the input device 134 via the input panels 50, 60, 61, 62, and the like. Based on the received input results, the processing circuitry 150 establishes the settings about the three or more pulse sequences including the first pulse sequence, the second pulse sequence, and the third pulse sequence.

The sequence controlling circuitry 120 executes the three or more pulse sequences for which the setting was established. By employing the calculating function 140, the processing circuitry 150 extracts the signals related to the plurality of types of fat, based on the pieces of data obtained from the three or more pulse sequences executed by the sequence controlling circuitry 120.

Other Embodiments

Possible embodiments are not limited to the embodiments described above.

In the embodiments above, the example is explained in which the sequence controlling circuitry 120 executes the pulse sequence three times; however, possible embodiments are not limited to this example. The number of pulse sequences executed by the sequence controlling circuitry 120 may be two or smaller, or conversely, may be four or larger, depending on the targets to be imaged.

Further, in the embodiments, the example is explained in which the magnetic resonance imaging process is performed for the purpose of rendering the signals of water and the fats; however, the targets to be imaged may be other substances besides water and fats.

Computer Programs

Further, the instructions indicated in the processing procedures explained in the embodiments above may be executed on the basis of a computer program (hereinafter, "program") realized with software. By causing a generic computer to store the program therein in advance and to read the program, it is also possible to achieve the same advantageous effects as those achieved by the magnetic resonance imaging apparatus 100 according to any of the embodiments described above. The instructions described in the embodiments above may be recorded as a computer-executable program on a magnetic disk (a flexible disk, a hard disk, or the like), an optical disk (a Compact Disk Read-Only Memory [CD-ROM], a Compact Disc Recordable [CD-R], a Compact Disk Rewritable [CD-RW], a Digital Versatile Disk Read-Only Memory [DVD-ROM], a DVD Recordable [DVD±R], a DVD Rewritable [DVD±RW], or the like), a semiconductor memory, or a similar recording medium. As long as the storage medium is readable by a computer or an embedded system, any storage format may be used. By reading the program from such a recording medium and causing a CPU to execute the instructions written in the program based on the program, the computer is able to realize the same operations as those performed by the magnetic resonance imaging apparatus 100 in any of the embodiments described above. Further, when obtaining or reading the program, the computer may obtain or read the program via a network.

Further, a part of the processes that realize any of the embodiments described above may be performed by an Operating System (OS) working in a computer or middleware (MW) such as database management software or a network, based on the instructions in the program installed in a computer or an embedded system from a storage medium. Furthermore, the storage medium does not necessarily have to be a medium independent of the computer or the embedded system and may be a storage medium downloading and storing or temporarily storing therein the program transmitted via a Local Area Network (LAN), the Internet, or the like. Also, the number of storage media being used does not necessarily have to be one. The storage medium according to the embodiments includes the situation where the processes according to the embodiments are executed from two or more media. The medium or media can have any configuration.

The computer or the embedded system according to the embodiments is configured to execute the processes in the embodiments described above on the basis of the program stored in the storage medium and may be realized with any configuration that uses a single apparatus such as a personal computer, a microcomputer or the like, or a system in which a plurality of apparatuses are connected together via a network. Furthermore, the computer according to the embodiments does not necessarily have to be a personal computer, and may be an arithmetic processing device or a microcomputer included in an information processing device, or the like. The term "computer" is a generic term for any of various devices and apparatuses that are each able to realize the functions described in the embodiments by using the program.

According to at least one aspect of the embodiments described above, it is possible to render the signals of the plurality of types of fat.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus, comprising:
   sequence controlling circuitry configured to acquire a first piece of data by executing a first pulse sequence having a first Echo Time (TE) value, to acquire a second piece of data by executing a second pulse sequence having a second TE value different from the first TE value, and to acquire a third piece of data by executing a third pulse sequence having a third TE value different from the first and the second TE values, wherein the first pulse sequence, the second pulse sequence, and the third pulse sequence are executed such that a center frequency is equal to a frequency corresponding to a chemical shift of a fat, and wherein the second pulse sequence is executed such that the second TE value causes a signal of protons of a first fat and a signal of protons of a second fat to have phases opposite to each other; and
   processing circuitry configured to extract a signal related to water, a signal related to the first fat, and a signal related to the second fat, based on the first piece of data, the second piece of data, and the third piece of data, and based on values of a chemical shift of the water, a chemical shift of the first fat, and a chemical shift of the second fat;
   wherein the sequence controlling circuitry is further configured to
      execute the first pulse sequence by using the first TE value that causes a signal of the first fat and a signal of the second fat to be in-phase with each other,
      execute the second pulse sequence by using the second TE value that causes the signal of the first fat and the signal of the second fat to be out of phase with each other, and
      execute the third pulse sequence by using the third TE value that causes the signal of the first fat and the signal of the second fat to be out of phase with each other, and
   the sequence controlling circuitry is configured to execute only three pulse sequences, which are the first pulse sequence, the second pulse sequence, and the third pulse sequence.

2. The magnetic resonance imaging apparatus according to claim 1, wherein the sequence controlling circuitry is further configured to execute the first pulse sequence, the second pulse sequence, and the third pulse sequence as a linked one acquisition while maintaining a receiver gain at a same level.

3. The magnetic resonance imaging apparatus according to claim 1, wherein the processing circuitry is further configured to extract the signal related to the water, the signal related to the first fat, and the signal related to the second fat, based on values of a chemical shift of the water, a chemical shift of the first fat, and a chemical shift of the second fat.

4. The magnetic resonance imaging apparatus according to claim 1, wherein the sequence controlling circuitry is further configured to execute the first pulse sequence, the second pulse sequence, and the third pulse sequence such that the center frequency is equal to the frequency corresponding to a chemical shift of the fat, wherein the fat is aliphatic fat.

5. The magnetic resonance imaging apparatus according to claim 1, wherein the processing circuitry is further configured to generate one selected from between a two-dimensional image and a three-dimensional image, based on the signal related to the water, the signal related to the first fat, and the signal related to the second fat.

6. The magnetic resonance imaging apparatus according to claim 1, wherein
the processing circuitry is further configured to receive, from a user, an input indicating types of the first fat and the second fat and, based on a result of the received input, and establish a setting about the first pulse sequence, the second pulse sequence, and the third pulse sequence, and
the sequence controlling circuitry is further configured to execute the first pulse sequence, the second pulse sequence, and the third pulse sequence, while maintaining a receiver gain at a same level.

7. The magnetic resonance imaging apparatus according to claim 1, wherein
the processing circuitry is further configured to receive, from a user, an input indicating a plurality of types of fat including an input indicating types of the first fat and the second fat and, based on a result of the received input, and establish a setting about three or more pulse sequences including the first pulse sequence, the second pulse sequence, and the third pulse sequence,
the sequence controlling circuitry is further configured to execute the three or more pulse sequences, and
the processing circuitry is further configured to extract signals each related to a different one of the plurality of types of fat, based on pieces of data obtained from the three or more pulse sequences executed by the sequence controlling circuitry.

8. A magnetic resonance imaging method implemented by a magnetic resonance imaging apparatus, the method comprising:
acquiring a first piece of data by executing a first pulse sequence having a first Echo Time (TE) value; acquiring a second piece of data by executing a second pulse sequence having a second TE value different from the first TE value, wherein the second TE value causes a signal of protons of a first fat and a signal of protons of a second fat to have phases opposite to each other;
acquiring a third piece of data by executing a third pulse sequence having a third TE value different from the first and the second TE values, wherein the first pulse sequence, the second pulse sequence, and the third pulse sequence are executed such that a center frequency is equal to a frequency corresponding to a chemical shift of a fat; and
extracting a signal related to water, a signal related to the first fat, and a signal related to the second fat, based on the first piece of data, the second piece of data, and the third piece of data, and based on values of a chemical shift of the water, a chemical shift of the first fat, and a chemical shift of the second fat;
wherein the method further comprises
executing the first pulse sequence by using the first TE value that causes a signal of the first fat and a signal of the second fat to be in-phase with each other,
executing the second pulse sequence by using the second TE value that causes the signal of the first fat and the signal of the second fat to be out of phase with each other, and
executing the third pulse sequence by using the third TE value that causes the signal of the first fat and the signal of the second fat to be out of phase with each other; and
the method comprises executing only three pulse sequences, which are the first pulse sequence, the second pulse sequence and the third pulse sequence.

9. The magnetic resonance imaging method according to claim 7, wherein the fat is aliphatic fat.

10. A magnetic resonance imaging apparatus, comprising:
sequence controlling circuitry configured to acquire a first piece of data by executing a first pulse sequence having a first Echo Time (TE) value, to acquire a second piece of data by executing a second pulse sequence having a second TE value different from the first TE value, and to acquire a third piece of data by executing a third pulse sequence having a third TE value different from the first and the second TE values, wherein the first pulse sequence, the second pulse sequence, and the third pulse sequence are executed such that a center frequency is equal to a frequency corresponding to a chemical shift of a fat; and
processing circuitry configured to extract a signal related to water, a signal related to a first fat, and a signal related to a second fat, based on the first piece of data, the second piece of data, and the third piece of data, and based on values of a chemical shift of the water, a chemical shift of the first fat, and a chemical shift of the second fat;
wherein the second pulse sequence is executed such that the second TE value causes a signal of aliphatic protons and a signal of olefinic fat protons to have phases opposite to each other;
the sequence controlling circuitry is further configured to execute the first pulse sequence by using the first TE value that causes a signal of the first fat and a signal of the second fat to be in-phase with each other,
execute the second pulse sequence by using the second TE value that causes the signal of the first fat and the signal of the second fat to be out of phase with each other, and
execute the third pulse sequence by using the third TE value that causes the signal of the first fat and the signal of the second fat to be out of phase with each other; and
the sequence controlling circuitry is configured to execute only three pulse sequences, which are the first pulse sequence, the second pulse sequence, and the third pulse sequence.

11. A magnetic resonance imaging apparatus, comprising:
sequence controlling circuitry configured to acquire a first piece of data by executing a first pulse sequence having a first Echo Time (TE) value, to acquire a second piece of data by executing a second pulse sequence having a second TE value different from the first TE value, and to acquire a third piece of data by executing a third pulse sequence having a third TE value different from the first and the second TE values, wherein the first pulse sequence, the second pulse sequence, and the third pulse sequence are executed such that a center frequency is equal to a frequency corresponding to a chemical shift of a fat; and processing circuitry configured to extract a signal related to water, a signal related to a first fat, and a signal related to a second fat, based on the first piece of data, the second piece of data, and the third piece of data, and based on values of a chemical shift of the water, a chemical shift of the first fat, and a chemical shift of the second fat;

wherein the second pulse sequence is executed such that the second TE value causes a signal of aliphatic protons and a signal of unsaturated fat protons to have phases opposite to each other;

the sequence controlling circuitry is further configured to
execute the first pulse sequence by using the first TE value that causes a signal of the first fat and a signal of the second fat to be in-phase with each other,
execute the second pulse sequence by using the second TE value that causes the signal of the first fat and the signal of the second fat to be out of phase with each other, and
execute the third pulse sequence by using the third TE value that causes the signal of the first fat and the signal of the second fat to be out of phase with each other; and the sequence controlling circuitry is configured to execute only three pulse sequences, which are the first pulse sequence, the second pulse sequence, and the third pulse sequence.

12. A magnetic resonance imaging apparatus, comprising:
sequence controlling circuitry configured to acquire a first piece of data by executing a first pulse sequence having a first Echo Time (TE) value, to acquire a second piece of data by executing a second pulse sequence having a second TE value different from the first TE value, and to acquire a third piece of data by executing a third pulse sequence having a third TE value different from the first and the second TE values, wherein the first pulse sequence, the second pulse sequence, and the third pulse sequence are executed such that a center frequency is equal to a frequency corresponding to a chemical shift of a fat; and processing circuitry configured to extract a signal related to water, a signal related to a first fat, and a signal related to a second fat, based on the first piece of data, the second piece of data, and the third piece of data, and based on values of a chemical shift of the water, a chemical shift of the first fat, and a chemical shift of the second fat;

wherein the second pulse sequence is executed such that the second TE value causes a signal of aliphatic protons and a signal of polyunsaturated fat protons to have phases opposite to each other;

the sequence controlling circuitry is further configured to
execute the first pulse sequence by using the first TE value that causes a signal of the first fat and a signal of the second fat to be in-phase with each other,
execute the second pulse sequence by using the second TE value that causes the signal of the first fat and the signal of the second fat to be out of phase with each other, and
execute the third pulse sequence by using the third TE value that causes the signal of the first fat and the signal of the second fat to be out of phase with each other; and the sequence controlling circuitry is configured to execute only three pulse sequences, which are the first pulse sequence, the second pulse sequence, and the third pulse sequence.

13. A magnetic resonance imaging method implemented by a magnetic resonance imaging apparatus, the method comprising:
acquiring a first piece of data by executing a first pulse sequence having a first Echo Time (TE) value;
acquiring a second piece of data by executing a second pulse sequence having a second TE value different from the first TE value;
acquiring a third piece of data by executing a third pulse sequence having a third TE value different from the first and the second TE values, wherein the first pulse sequence, the second pulse sequence, and the third pulse sequence are executed such that a center frequency is equal to a frequency corresponding to a chemical shift of a fat; and
extracting a signal related to water, a signal related to a first fat, and a signal related to a second fat, based on the first piece of data, the second piece of data, and the third piece of data,
wherein the second pulse sequence is executed such that the second TE value causes a signal of aliphatic protons and a signal of olefinic fat protons to have phases opposite to each other, based on values of a chemical shift of the water, a chemical shift of the first fat, and a chemical shift of the second fat; and
the method further comprises
executing the first pulse sequence by using the first TE value that causes a signal of the first fat and a signal of the second fat to be in-phase with each other,
executing the second pulse sequence by using the second TE value that causes the signal of the first fat and the signal of the second fat to be out of phase with each other, and
executing the third pulse sequence by using the third TE value that causes the signal of the first fat and the signal of the second fat to be out of phase with each other; and
the method comprises executing only three pulse sequences, which are the first pulse sequence, the second pulse sequence and the third pulse sequence.

14. A magnetic resonance imaging method implemented by a magnetic resonance imaging apparatus, the method comprising:
acquiring a first piece of data by executing a first pulse sequence having a first Echo Time (TE) value;
acquiring a second piece of data by executing a second pulse sequence having a second TE value different from the first TE value;
acquiring a third piece of data by executing a third pulse sequence having a third TE value different from the first and the second TE values, wherein the first pulse sequence, the second pulse sequence, and the third pulse sequence are executed such that a center frequency is equal to a frequency corresponding to a chemical shift of a fat; and
extracting a signal related to water, a signal related to a first fat, and a signal related to a second fat, based on the first piece of data, the second piece of data, and the third piece of data, and based on values of a chemical shift of the water, a chemical shift of the first fat, and a chemical shift of the second fat;
wherein the second pulse sequence is executed such that the second TE value causes a signal of aliphatic protons and a signal of unsaturated fat protons to have phases opposite to each other;
the method further comprises executing the first pulse sequence by using the first TE value that causes a signal of the first fat and a signal of the second fat to be in-phase with each other, executing the second pulse sequence by using the second TE value that causes the signal of the first fat and the signal of the second fat to be out of phase with each other, and executing the third pulse sequence by using the third TE value that causes the signal of the first fat and the signal of the second fat to be out of phase with each other; and the method comprises executing only three pulse sequences, which are the first pulse sequence, the second pulse sequence and the third pulse sequence.

15. A magnetic resonance imaging method implemented by a magnetic resonance imaging apparatus, the method comprising:

acquiring a first piece of data by executing a first pulse sequence having a first Echo Time (TE) value;

acquiring a second piece of data by executing a second pulse sequence having a second TE value different from the first TE value;

acquiring a third piece of data by executing a third pulse sequence having a third TE value different from the first and the second TE values, wherein the first pulse sequence, the second pulse sequence, and the third pulse sequence are executed such that a center frequency is equal to a frequency corresponding to a chemical shift of a fat; and extracting a signal related to water, a signal related to a first fat, and a signal related to a second fat, based on the first piece of data, the second piece of data, and the third piece of data, and based on values of a chemical shift of the water, a chemical shift of the first fat, and a chemical shift of the second fat;

wherein the second pulse sequence is executed such that the second TE value causes a signal of aliphatic protons and a signal of polyunsaturated fat protons to have phases opposite to each other;

the method further comprises executing the first pulse sequence by using the first TE value that causes a signal of the first fat and a signal of the second fat to be in-phase with each other, executing the second pulse sequence by using the second TE value that causes the signal of the first fat and the signal of the second fat to be out of phase with each other, and executing the third pulse sequence by using the third TE value that causes the signal of the first fat and the signal of the second fat to be out of phase with each other; and the method comprises executing only three pulse sequences, which are the first pulse sequence, the second pulse sequence and the third pulse sequence.

* * * * *